(12) United States Patent
Keller et al.

(10) Patent No.: US 8,843,217 B1
(45) Date of Patent: Sep. 23, 2014

(54) COMBINED VESTIBULAR AND COCHLEAR IMPLANT AND METHOD

(71) Applicant: Lockheed Martin Corporation, Bethesda, MD (US)

(72) Inventors: Matthew D. Keller, Kirkland, WA (US); Brandon P. Schmidt, Liverpool, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 14/027,152

(22) Filed: Sep. 13, 2013

(51) Int. Cl.
  *A61N 1/00* (2006.01)
  *A61B 5/04* (2006.01)
  *A61N 5/06* (2006.01)
  *A61N 1/36* (2006.01)

(52) U.S. Cl.
  CPC .......... *A61N 5/0622* (2013.01); *A61N 1/36032* (2013.01)
  USPC ................................ 607/137; 607/3; 600/379

(58) Field of Classification Search
  USPC ....................................... 607/3, 137; 600/379
  See application file for complete search history.

(56) References Cited

U.S. PATENT DOCUMENTS

| | | | |
|---|---|---|---|
| 4,558,703 | A | 12/1985 | Mark |
| 4,596,992 | A | 6/1986 | Hornbeck |
| 4,928,695 | A | 5/1990 | Goldman et al. |
| 5,419,312 | A | 5/1995 | Arenberg et al. |
| 6,330,388 | B1 | 12/2001 | Bendett et al. |
| 6,358,272 | B1 | 3/2002 | Wilden |
| 6,493,476 | B2 | 12/2002 | Bendett |
| 6,546,291 | B2 | 4/2003 | Merfeld et al. |
| 6,636,678 | B1 | 10/2003 | Bendett et al. |
| 6,690,873 | B2 | 2/2004 | Bendett et al. |
| 6,748,275 | B2 | 6/2004 | Lattner et al. |
| 6,921,413 | B2 | 7/2005 | Mahadevan-Jansen et al. |
| 7,004,645 | B2 | 2/2006 | Lemoff et al. |
| 7,010,356 | B2 | 3/2006 | Jog et al. |
| 7,031,363 | B2 | 4/2006 | Biard et al. |
| 7,116,886 | B2 | 10/2006 | Colgan et al. |
| 7,190,993 | B2 | 3/2007 | Sharma et al. |
| 7,225,028 | B2 | 5/2007 | Della Santina et al. |
| 7,391,561 | B2 | 6/2008 | Di Teodoro et al. |

(Continued)

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

(Continued)

*Primary Examiner* — Nicole F Lavert
(74) *Attorney, Agent, or Firm* — Charles A. Lemaire; Jonathan M. Rixen; Lemaire Patent Law Firm, P.L.L.C.

(57) ABSTRACT

Apparatus and method for triggering nerve-action potentials (NAPs) in each of a plurality of cochlear neurons in a cochlea of a person and in each one of a plurality of vestibular neurons in a vestibular organ of the person in order to provide auditory and balance sensations for the person, the method including generating a first plurality of light signals that stimulate a NAP in the selected cochlear neuron; delivering the first plurality of light signals to the selected cochlear neuron from within the cochlea; generating a second plurality of light signals that stimulate a NAP in the selected vestibular neuron; delivering the second plurality of light signals to the selected vestibular neuron from within the vestibular organ; and selectively controlling the first and second plurality of light signals to optically stimulate the selected cochlear and vestibular neuron in order to trigger NAPs of the selected cochlear and vestibular neuron.

20 Claims, 13 Drawing Sheets

(56) References Cited

U.S. PATENT DOCUMENTS

| | | | |
|---|---|---|---|
| RE40,587 E | 11/2008 | McKinnon | |
| 7,488,341 B2 | 2/2009 | Merfeld | |
| 7,736,382 B2 | 6/2010 | Webb et al. | |
| 7,747,318 B2 | 6/2010 | John et al. | |
| 7,756,588 B2 | 7/2010 | Jog et al. | |
| 7,787,170 B2 | 8/2010 | Patel et al. | |
| 7,797,029 B2 | 9/2010 | Gibson et al. | |
| 7,801,601 B2 | 9/2010 | Maschino et al. | |
| 7,833,257 B2 | 11/2010 | Walsh, Jr. et al. | |
| 7,883,535 B2 | 2/2011 | Cantin et al. | |
| 7,883,536 B1 | 2/2011 | Bendett et al. | |
| 7,988,688 B2 | 8/2011 | Webb et al. | |
| 8,012,189 B1 | 9/2011 | Webb et al. | |
| 8,160,696 B2 | 4/2012 | Bendett et al. | |
| 8,372,127 B2 | 2/2013 | Merfeld | |
| 8,396,570 B2 | 3/2013 | Dadd et al. | |
| 8,475,506 B1 | 7/2013 | Bendett et al. | |
| 8,498,699 B2 | 7/2013 | Wells et al. | |
| 8,515,215 B2 | 8/2013 | Younge et al. | |
| 2007/0053996 A1 | 3/2007 | Boyden et al. | |
| 2007/0054319 A1 | 3/2007 | Boyden et al. | |
| 2007/0261127 A1 | 11/2007 | Boyden et al. | |
| 2008/0077200 A1 | 3/2008 | Bendett et al. | |
| 2009/0099441 A1 | 4/2009 | Giszter et al. | |
| 2009/0177247 A1 | 7/2009 | Neal et al. | |
| 2010/0049180 A1 | 2/2010 | Wells et al. | |
| 2010/0162109 A1 | 6/2010 | Chatterjee et al. | |
| 2010/0292758 A1 | 11/2010 | Lee et al. | |
| 2011/0295331 A1 | 12/2011 | Wells et al. | |
| 2011/0295345 A1 | 12/2011 | Wells et al. | |
| 2012/0022616 A1 | 1/2012 | Garnham et al. | |
| 2013/0013030 A1 | 1/2013 | Mahadevan-Jansen et al. | |
| 2013/0023967 A1 | 1/2013 | Stafford et al. | |

OTHER PUBLICATIONS

Arora, Komal, et al., "Electrical stimulation rate effects on speech perception in cochlear implants", "International Journal of Audiology", 2009, pp. 561-567, vol. 48.

Fork, Richard L., "Laser Stimulation of Nerve Cells in Aplysia", "Science, New Series", Mar. 5, 1971, pp. 907-908, vol. 171, No. 3974.

Fu, Qian-Jie, et al., "Effect of Stimulation Rate on Phoneme Recognition by Nucleus-22 Cochlear Implant Listeners", "J. Acoust. Soc. Am.", Jan. 2000, pp. 589-597, vol. 107, No. 1.

Fu, Qian-Jie, et al., "Effects of Dynamic Range and Amplitude Mapping on Phoneme Recognition in Nucleus-22 Cochlear Implant Users", "Ear and Hearing", 2000, pp. 227-235, vol. 21.

Heinz, Michael G., et al., "Response Growth with Sound Level in Auditory-Nerve Fibers After Noise-Induced Hearing Loss", "J. Neurophysiology", 2004, pp. 784-795, vol. 91.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, p. 1108-1114, vol. 54, No. 6(1).

Littlefield, Philip D., et al., "Laser Stimulation of Single Auditory Nerve Fibers", "Laryngoscope", Oct. 2010, pp. 2071-2082, vol. 120.

Loizou, Philipos C., "Speech Processing in Vocoder-Centric Cochlear Implants", "Adv. Oto-Rhino-Laryngolog", 2006, pp. 109-143, vol. 64.

McKay, et al., "Loudness Perception with Pulsatile Electrical Stimulation: The Effect of Interpulse Intervals", 1998.

McKay, et al., "Loudness Summation for Pulsatile Electrical Stimulation of the Cochlea: Effects of Rate, Electrode Separation, Level, an", "J. Acoust. Soc. Am.", Sep. 2001, pp. 1514-1524, vol. 110.

Moller, Aage R., "History of Cochlear Implants and Auditory Brainstem Implants", "Adv Otorhinolaryngol. Basel, Karger", 2006, pp. 1-10, vol. 64.

Nelson, et al., "Intensity Discrimination as a Function of Stimulus Level with Electric Stimulation", "J. Acoust. Soc. Am.", Oct. 1996, pp. 2393-2414, vol. 100.

Omran, Sherif Abdellatif, et al., "Semitone Frequency Mapping to Improve Music Representation for Nucleus Cochlear Implants", "EURASIP Journal on Audio, Speech, and Music Processing", 2011, vol. 2011:2.

Vandali, et al., "Speech Perception as a Function of Electrical Stimulation Rate: Using the Nucleus 24 Cochlear Implant", Dec. 2000.

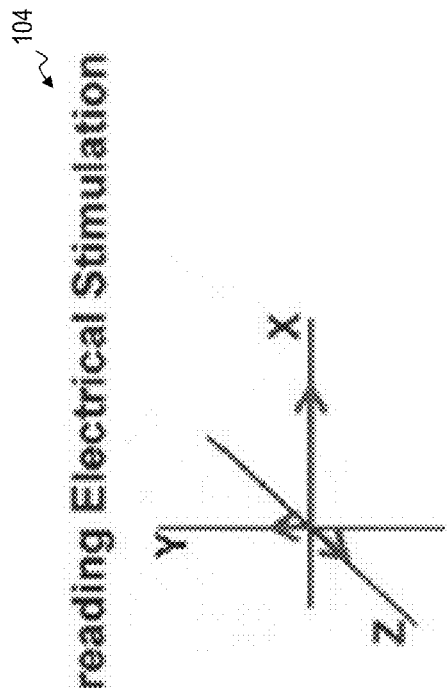
FIG. 1D-1
(A) Head Rotation    (B) Spreading Electrical Stimulation
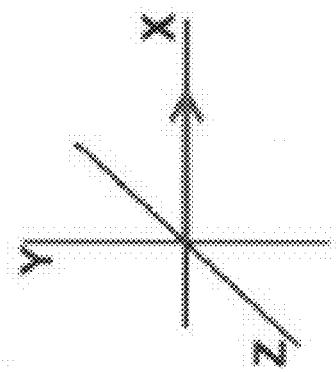
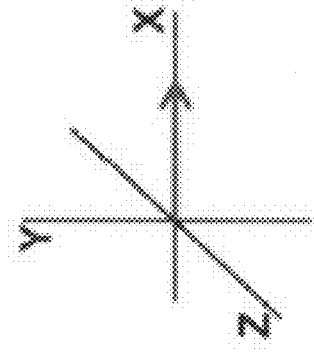
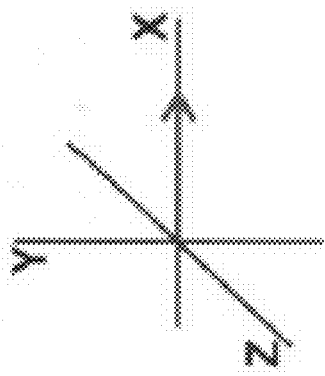
FIG. 1D-2
(A) Head rotation    (B) Precise Optical Stimulation

FIG. 3

| VI PORTION 210 | CI PORTION 220 | | | |
|---|---|---|---|---|
| | INS | HYBRID | ELECTRICAL STIM | OPTOGENETICS |
| INS | YES | YES | YES | YES |
| HYBRID | YES | YES | YES | YES |
| ELECTRICAL STIM | YES | YES | YES | YES |
| OPTOGENETICS | YES | YES | YES | YES |

301

COMBINED VESTIBULAR AND COCHLEAR IMPLANT AND METHOD

CROSS-REFERENCE TO RELATED APPLICATIONS

This invention is related to:

U.S. Pat. No. 7,736,382 issued Jun. 15, 2010 to James S. Webb et al., titled "APPARATUS FOR OPTICAL STIMULATION OF NERVES AND OTHER ANIMAL TISSUE,"

U.S. Pat. No. 7,883,536 issued Feb. 8, 2011 to Mark P. Bendett et al., titled "HYBRID OPTICAL-ELECTRICAL PROBES,"

U.S. Pat. No. 7,988,688 issued Aug. 2, 2011 to James S. Webb et al., titled "MINIATURE APPARATUS AND METHOD FOR OPTICAL STIMULATION OF NERVES AND OTHER ANIMAL TISSUE,"

U.S. patent application Ser. No. 11/948,912 filed Nov. 30, 2007 by James S. Webb et al., titled "APPARATUS AND METHOD FOR CHARACTERIZING OPTICAL SOURCES USED WITH HUMAN AND ANIMAL TISSUES,"

U.S. patent application Ser. No. 11/536,642 filed Sep. 28, 2006 by Mark P. Bendett et al., titled "APPARATUS AND METHOD FOR STIMULATION OF NERVES AND AUTOMATED CONTROL OF SURGICAL INSTRUMENTS,"

U.S. Pat. No. 8,012,189 issued Sep. 6, 2011 to James S. Webb et al., titled "VESTIBULAR IMPLANT USING OPTICAL STIMULATION OF NERVES,"

U.S. Pat. No. 8,317,848 issued Nov. 27, 2012 to James S. Webb et al., titled "VESTIBULAR IMPLANT AND METHOD FOR OPTICAL STIMULATION OF NERVES,"

U.S. patent application Ser. No. 13/671,379 filed Nov. 27, 2012 by James S. Webb et al., titled "METHOD AND SYSTEM FOR OPTICAL STIMULATION OF VESTIBULAR NERVES" (which issued as U.S. Pat. No. 8,551,150 on Oct. 8, 2013), U.S. patent application Ser. No. 12/191,301 filed Aug. 13, 2008 by Mark P. Bendett et al., titled "VCSEL ARRAY STIMULATOR APPARATUS AND METHOD FOR LIGHT STIMULATION OF BODILY TISSUES" (which issued as U.S. Pat. No. 8,475,506 on Jul. 2, 2013), U.S. Pat. No. 8,160,696 issued Apr. 17, 2012 to Mark P. Bendett et al., titled "NERVE STIMULATOR AND METHOD USING SIMULTANEOUS ELECTRICAL AND OPTICAL SIGNALS,"

U.S. patent application Ser. No. 13/013,816 filed Jan. 26, 2011 by Jonathon D. Wells et al., titled "NERVE STIMULATOR AND METHOD USING SIMULTANEOUS ELECTRICAL AND OPTICAL SIGNALS" (which issued as U.S. Pat. No. 8,498,699 on Jul. 30, 2013), U.S. patent application Ser. No. 12/693,427 filed Jan. 25, 2010 by Daniel J. Lee et al., titled "OPTICAL STIMULATION OF THE BRAINSTEM AND/OR MIDBRAIN, INCLUDING AUDITORY AREAS" (which issued as U.S. Pat. No. 8,744,570 on Jun. 3, 2014), U.S. patent application Ser. No. 12/890,602 filed Sep. 24, 2010 by Jonathon D. Wells et al., titled "LASER-BASED NERVE STIMULATORS FOR, E.G., HEARING RESTORATION IN COCHLEAR PROSTHESES" (which issued as U.S. Pat. No. 8,792,978 on Jul. 29, 2014), U.S. patent application Ser. No. 13/117,121 filed May 26, 2011 by Jonathon D. Wells et al., titled "IMPLANTABLE INFRARED NERVE STIMULATION DEVICES FOR PERIPHERAL AND CRANIAL NERVE INTERFACES,"

U.S. patent application Ser. No. 13/117,122 filed May 26, 2011 by Jonathon D. Wells et al., titled "CUFF APPARATUS AND METHOD FOR OPTICAL AND/OR ELECTRICAL NERVE STIMULATION OF PERIPHERAL NERVES" (which issued as U.S. Pat. No. 8,652,187 on Feb. 18, 2014), U.S. patent application Ser. No. 13/117,125 filed May 26, 2011 by Jonathon D. Wells et al., titled "NERVE-PENETRATING APPARATUS AND METHOD FOR OPTICAL AND/OR ELECTRICAL NERVE STIMULATION OF PERIPHERAL NERVES,"

U.S. patent application Ser. No. 13/117,118 filed May 26, 2011 by Jonathon D. Wells et al., titled "OPTICAL BUNDLE APPARATUS AND METHOD FOR OPTICAL AND/OR ELECTRICAL NERVE STIMULATION OF PERIPHERAL NERVES,"

U.S. Provisional Patent Application 61/349,810 filed May 28, 2010 by Jonathon D. Wells et al., titled "Implantable Infrared Nerve Stimulation Devices for Peripheral and Cranial Nerve Interfaces,"

U.S. Provisional Patent Application 61/386,461 filed Sep. 24, 2010 by Jonathon D. Wells et al., titled "Implantable Infrared Nerve Stimulation Devices for Peripheral and Cranial Nerve Interfaces,"

U.S. Provisional Patent Application 61/511,020 filed Jul. 22, 2011 by Ryan C. Stafford, titled "METHOD AND APPARATUS FOR OPTIMIZING AN OPTICALLY STIMULATING COCHLEAR IMPLANT,"

U.S. Provisional Patent Application 61/511,048 filed Jul. 23, 2011 by Ryan C. Stafford, titled "BROAD WAVELENGTH PROFILE TO HOMOGENIZE THE ABSORPTION PROFILE IN OPTICAL STIMULATION OF THE COCHLEA,"

U.S. Provisional Patent Application 61/511,050 filed Jul. 23, 2011 by Ryan C. Stafford et al., titled "OPTICAL COCHLEAR IMPLANT WITH ELECTRODE(S) AT THE APICAL END FOR STIMULATION OF APICAL SPIRAL GANGLION CELLS OF THE COCHLEA,"

U.S. patent application Ser. No. 13/555,091 filed Jul. 21, 2012 by Ryan C. Stafford et al., titled "OPTICAL-STIMULATION COCHLEAR IMPLANT WITH ELECTRODE(S) AT THE APICAL END FOR ELECTRICAL STIMULATION OF APICAL SPIRAL GANGLION CELLS OF THE COCHLEA,"

U.S. patent application Ser. No. 13/555,092 filed Jul. 21, 2012 by Ryan C. Stafford, titled "BROAD WAVELENGTH PROFILE TO HOMOGENIZE THE ABSORPTION PROFILE IN OPTICAL STIMULATION OF NERVES,"

U.S. patent application Ser. No. 13/555,093 filed Jul. 21, 2012 by Ryan C. Stafford et al., titled "INDIVIDUALLY OPTIMIZED PERFORMANCE OF OPTICALLY STIMULATING COCHLEAR IMPLANTS,"

U.S. patent application Ser. No. 13/555,094 filed Jul. 21, 2012 by Ryan C. Stafford et al., titled "COCHLEAR IMPLANT AND METHOD ENABLING ENHANCED MUSIC PERCEPTION" (which issued as U.S. Pat. No. 8,747,447 on Jun. 10, 2014), U.S. patent application Ser. No. 13/555,095 filed Jul. 21, 2012 by Ryan C. Stafford et al., titled "COCHLEAR IMPLANT USING OPTICAL STIMULATION WITH ENCODED INFORMATION DESIGNED TO LIMIT HEATING EFFECTS,"

U.S. patent application Ser. No. 13/555,097 filed Jul. 21, 2012 by Ryan C. Stafford et al., titled "OPTICAL PULSE-WIDTH MODULATION USED IN AN OPTICAL-STIMULATION COCHLEAR IMPLANT,"

U.S. patent application Ser. No. 13/555,098 filed Jul. 21, 2012 by Ryan C. Stafford et al., titled "OPTIMIZED STIMU- LATION RATE OF AN OPTICALLY STIMULATING COCHLEAR IMPLANT;" and U.S. patent application Ser. No. 13/841,831 filed Mar. 15, 2013 by Ryan C. Stafford et al., titled "METHOD AND APPARATUS TO PROVIDE DIAGNOSTICS FOR COCHLEAR-IMPLANT PERFORMANCE IMPROVEMENT," each of which is incorporated herein by reference in its entirety.

FIELD OF THE INVENTION

The invention relates generally to tissue optics (interactions of light with human or animal tissue), and more particularly to methods and implantable apparatus for stimulating nerves of the inner ear in animals, for example, using an implantable device in medical treatments for conditions of the vestibular and cochlear systems.

BACKGROUND OF THE INVENTION

Cochlear implants have successfully restored at least some hearing to approximately 200,000 people worldwide. As successful as these implants have been in restoring some function to the cochlea and the auditory portion of the inner ear, there currently is not a reliable treatment that addresses the other portion of the inner ear, the vestibular system. The vestibular system is responsible for providing balance to individuals. Millions of people worldwide suffer from balance disorders, leaving many of those with severe cases debilitated and unable to perform normal daily tasks. Several groups have begun investigation of an electrical prosthesis for the vestibular system but will likely be limited because of current spread within the vestibular space. Additionally, some early human recipients of electrical based vestibular implants have gone deaf after being implanted.

Many people would benefit from receiving both a cochlear implant and a vestibular implant if substantially all or all of the hair cells in the inner ear are damaged, thus disabling the auditory and balance senses of an individual. Often, implanting a device into the vestibular system or cochlear can damage the other system, leading to the need for treatment of that other system. Since the vestibular and cochlear systems both reside in the inner ear and are connected, a combined device would allow for effective treatment to be provided to each respective area. Additionally, the use of optical stimulation for one or both of the devices is likely to be more efficacious because infrared nerve stimulation or a hybrid infrared and electrical method is more spatially selective than electrical by itself due to the current spreading that happens during electrical stimulation.

U.S. Pat. No. 7,004,645 to Brian E. Lemoff et al. (hereinafter, "Lemoff et al."), titled "VCSEL ARRAY CONFIGURATION FOR A PARALLEL WDM TRANSMITTER", issued Feb. 28, 2006, and is incorporated herein by reference.

U.S. Pat. No. 7,031,363 to James R. Biard et al. (hereinafter, "Biard et al."), titled "LONG WAVELENGTH VCSEL DEVICE PROCESSING", issued Apr. 18, 2006, and is incorporated herein by reference.

U.S. Pat. No. 7,225,028 to Charles C. Della Santina et al. (hereinafter, "Della Santina et al."), titled "DUAL COCHLEAR/VESTIBULAR STIMULATOR WITH CONTROL SIGNALS DERIVED FROM MOTION AND SPEECH SIGNALS", issued May 29, 2007, and is incorporated herein by reference.

U.S. Pat. No. 7,488,341 to Daniel M. Merfeld (hereinafter, "Merfeld"), titled "METHOD FOR OPTICAL STIMULATION OF THE VESTIBULAR SYSTEM", issued Feb. 10, 2009, and is incorporated herein by reference.

U.S. Patent Application Publication 2006/0129210 to Daniel Cantin et al. (hereinafter, "Cantin et al."), titled "DEVICE AND METHOD FOR TRANSMITTING MULTIPLE OPTICALLY-ENCODED STIMULATION SIGNALS TO MULTIPLE CELL LOCATIONS", published Jun. 15, 2006, and is incorporated herein by reference.

U.S. Patent Application Publication 2007/0261127 to Edward S. Boyden et al. (hereinafter, "Boyden et al."), titled "LIGHT-ACTIVATED CATION CHANNEL AND USES THEREOF", published Nov. 8, 2007, and is incorporated herein by reference.

U.S. Patent Application Publication 2009/0093403 to Feng Zhang et al. (hereinafter, "Zhang et al."), titled "SYSTEMS, METHODS AND COMPOSITIONS FOR OPTICAL STIMULATION OF TARGET CELLS", published Apr. 9, 2009, and is incorporated herein by reference.

U.S. Patent Application Publication 2012/0022616 to Carolyn Garnham et al. (hereinafter, "Garnham et al."), titled "VESTIBULAR IMPLANT SYSTEM WITH INTERNAL AND EXTERNAL MOTION SENSORS", published Jan. 26, 2012, and is incorporated herein by reference.

U.S. Patent Application Publication 2013/0013030 to Anita Mahadevan-Jansen et al. (hereinafter, "Mahadevan-Jansen et al."), titled "METHOD AND APPARATUS OF PULSED INFRARED LIGHT FOR THE INHIBITION OF CENTRAL NERVOUS SYSTEM NEURONS", published Jan. 10, 2013, and is incorporated herein by reference.

Accordingly, there is a need in the art for improved methods and implantable apparatus to treat various vestibular and cochlear problems.

SUMMARY OF THE INVENTION

In some embodiments, the present invention provides infrared nerve stimulation to restore both hearing and balance function in a single device (in some such embodiments, the infrared nerve stimulation allows for more precise stimulation of nerves compared to electrical stimulation and the optical-based delivery avoids the spreading of current and artifacts from stimulation that are present with electrical stimulation). In some embodiments, the single device provides various combinations of electrical and optical stimulation to stimulate the cochlea and vestibular systems, including: infrared nerve stimulation, a hybrid of infrared nerve stimulation and electrical nerve stimulation, optogenetics, and electrical stimulation.

In some embodiments, the present invention provides a method for triggering nerve-action potentials (NAPs) in each one of a plurality of cochlear neurons in a cochlea of a person and in each one of a plurality of vestibular neurons in a vestibular organ of the person in order to provide auditory and balance sensations for the person, the method including generating a first plurality of light signals that, when applied to a selected one of the plurality of cochlear neurons, stimulate a NAP in the selected cochlear neuron; delivering the first plurality of light signals to the selected cochlear neuron from within the cochlea; generating a second plurality of light signals that, when applied to a selected one of the plurality of vestibular neurons, stimulate a NAP in the selected vestibular neuron; delivering, during a first period of time, the second plurality of light signals to the selected vestibular neuron from within the vestibular organ; and selectively controlling the first plurality and the second plurality of light signals to optically stimulate the selected cochlear neuron and the selected vestibular neuron in order to trigger NAPs of the selected cochlear neuron and the selected vestibular neuron.

In some embodiments, the present invention provides an apparatus for stimulating nerve-action potentials (NAPs) in each one of a plurality of cochlear neurons in a cochlea of a person and in each one of a plurality of vestibular neurons in a vestibular organ of the person in order to provide auditory and balance sensations for the person, the apparatus including a cochlear-implant portion, wherein the cochlear-implant portion includes a first plurality of independently controllable light sources that are configured to generate a first plurality of light signals, including a first light signal and a second light signal, that, when applied to a selected one of the plurality of cochlear neurons, each stimulate a nerve action potential (NAP) in the selected cochlear neuron, and a first transmission medium configured to transmit the first plurality of light signals from the first plurality of light sources to the selected cochlear neuron in order to trigger NAPs in the selected cochlear neuron; a vestibular-implant portion, wherein the vestibular-implant portion includes a second plurality of independently controllable light sources that are configured to generate a second plurality of light signals, including a third light signal and a fourth light signal, that, when applied to a selected one of the plurality of vestibular neurons of a vestibular system of the person, each stimulate a nerve action potential (NAP) in the selected vestibular neuron, and a second transmission medium configured to transmit the second plurality of light signals from the second plurality of light sources to the selected vestibular neuron in order to trigger NAPs in the selected vestibular neuron; and a controller operatively coupled to the cochlear-implant portion to selectively control the first plurality of light signals from each of the first plurality of light sources such that the first plurality of light signals provide controlled optical stimulation to the selected cochlear neuron in order to trigger nerve action potentials (NAPs) produced by the selected cochlear neuron, and wherein the controller is also operatively coupled to the vestibular-implant portion to selectively control the second plurality of light signals from each of the second plurality of light sources such that the second plurality of light signals provide controlled optical stimulation to the selected vestibular neuron in order to trigger nerve action potentials (NAPs) produced by the selected vestibular neuron.

BRIEF DESCRIPTION OF THE FIGURES

Each of the items shown in the following brief description of the drawings represents some embodiments of the present invention.

FIG. 1C-2 is a pair of graphs 103 illustrating the advantages of optical-based nerve stimulation of the cochlea.

FIG. 1D-1 is a pair of graphs 104 illustrating the limitations of electrical-only nerve stimulation of the vestibular system.

FIG. 1D-2 is a pair of graphs 105 illustrating the advantages of optical-based nerve stimulation of the vestibular system.

FIG. 3 is a table 301 showing the various combinations of inner-ear nerve stimulation that are possible with the combined VI portion 210 and CI portion 220 shown in FIGS. 2A-2C.

DETAILED DESCRIPTION OF THE INVENTION

Although the following detailed description contains many specifics for the purpose of illustration, a person of ordinary skill in the art will appreciate that many variations and alterations to the following details are within the scope of the invention. Very narrow and specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1A:
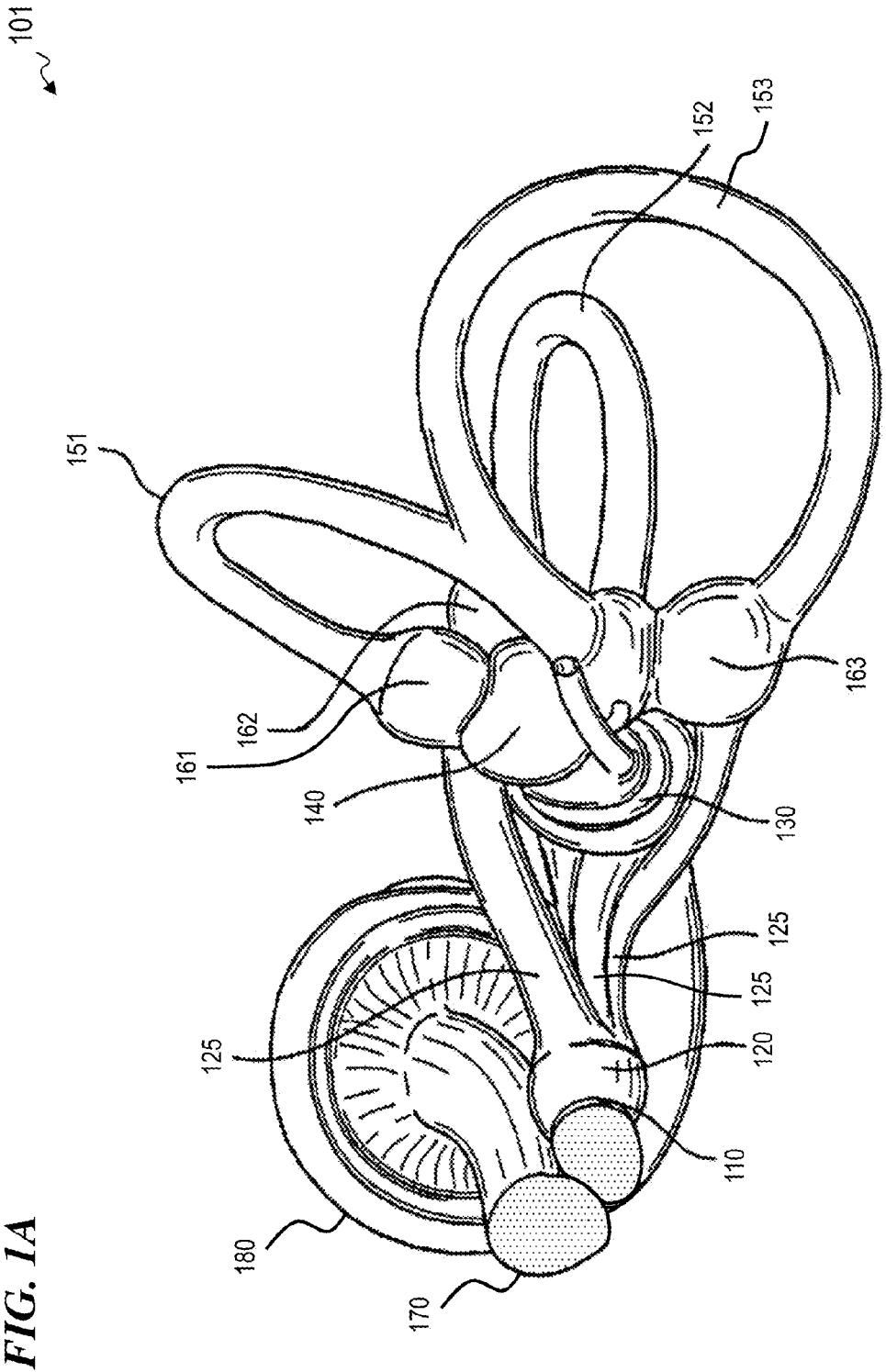
FIG. 1A is a perspective view of an inner-ear labyrinth of nerves and organs 101.

FIG. 1A is a perspective view of an inner-ear labyrinth of nerves and organs 101. The vestibular nerve 110 is an afferent nerve that carries impulses toward the central nervous system. The vestibular nerve branches 125 (including the anterior canal nerve, the posterior canal nerve, the lateral canal nerve, the utricular nerve, and the saccular nerve) join together at the vestibular ganglion 120. The vestibular portion of the inner-ear labyrinth includes the anterior semicircular canal 151 and anterior semicircular ampulla 161, lateral semicircular canal 152 and lateral semicircular ampulla 162, posterior semicircular canal 153 and posterior semicircular ampulla 163, the utricle 140, and the saccule 130. The cochlear portion of the inner-ear labyrinth includes the cochlea 180 and the cochlear nerve 170.

Figure 1B:
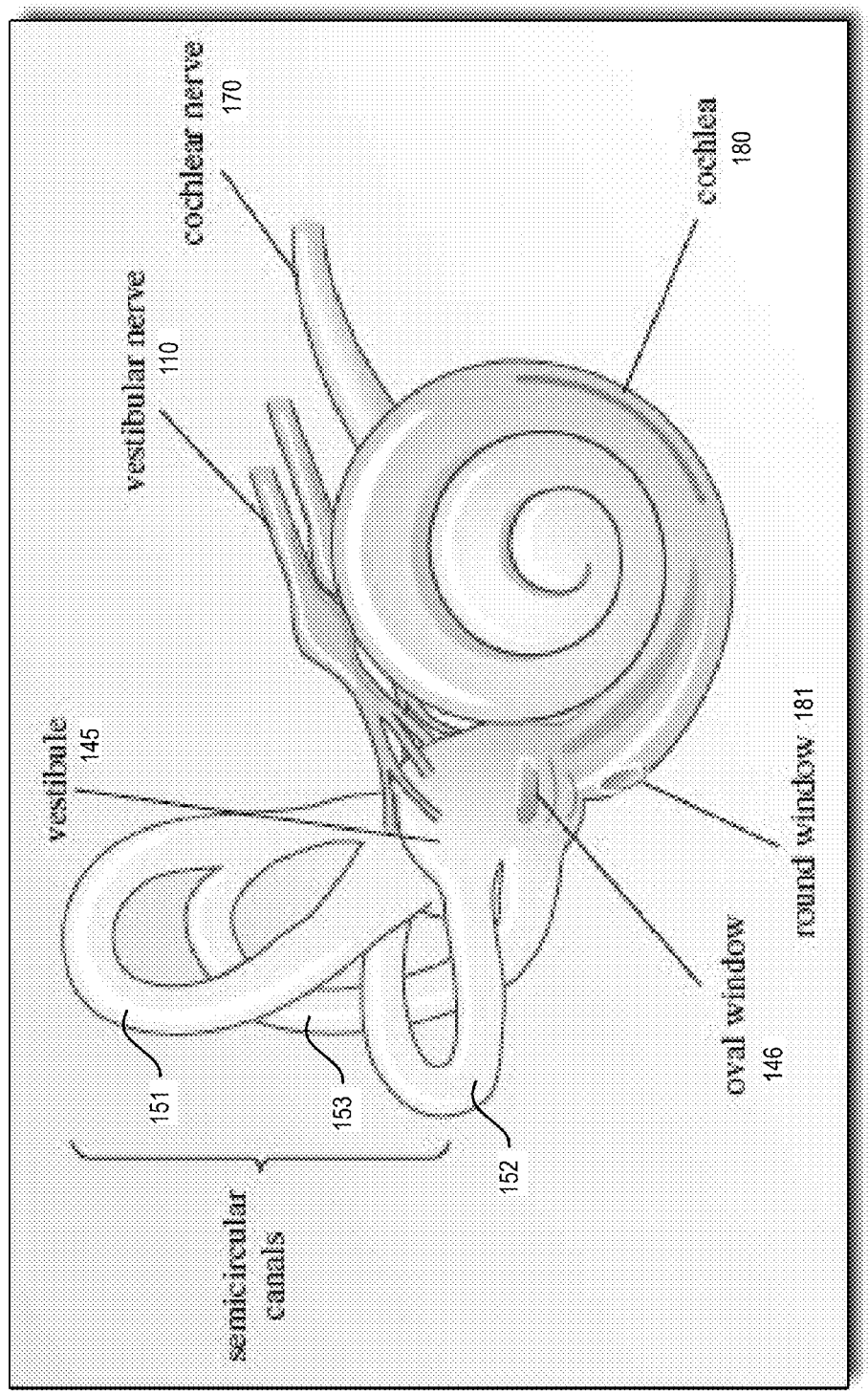
FIG. 1B is a perspective view of inner-ear labyrinth 101 as viewed from the side opposite that shown in FIG. 1A.

FIG. 1B is a perspective view of inner-ear labyrinth 101 as viewed from the side opposite that shown in FIG. 1A. The view of labyrinth 101 shown in FIG. 1B also differs from that shown in FIG. 1A because it shows the vestibule 145 (which contains saccule 130 and utricle 140 of FIG. 1A) and it shows oval window 146 and round window 181.

Figures 1, 1C:
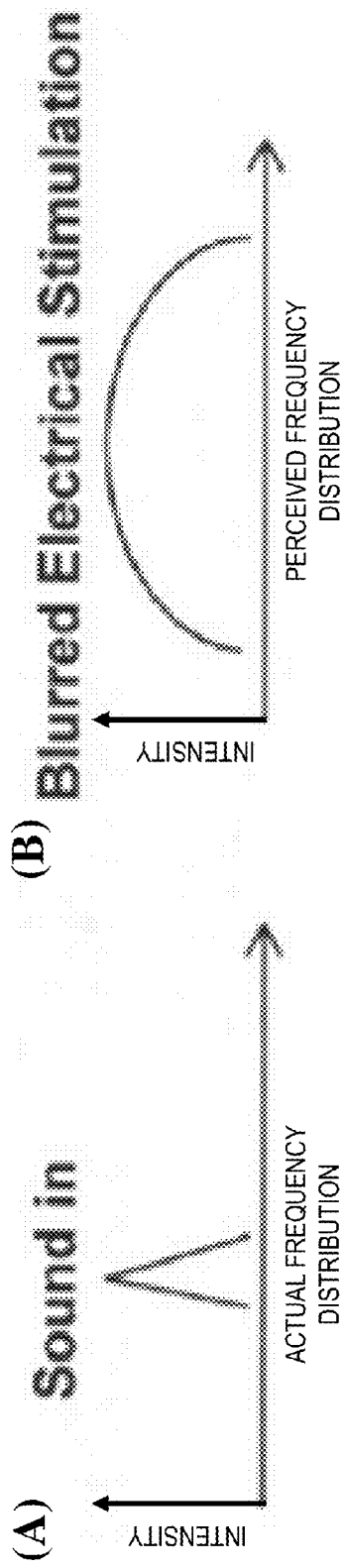
FIG. 1C-1 is a pair of graphs 102 illustrating the limitations of electrical-only nerve stimulation of the cochlea.

FIG. 1C-1 is a pair of graphs 102 illustrating the limitations of electrical-only nerve stimulation of the cochlea. Graph (A) of FIG. 1C-1 shows a sound signal (sound in) in terms of frequency distribution (x-axis) versus intensity (y-axis). Graph (B) of FIG. 1C-1 shows the perceived sense of sound for a person created by an electrical-only nerve stimulator that stimulates the cochlea of the person based on the sound signal of Graph (A) in FIG. 1C-1. As shown by Graph (B) of FIG. 1C-1, the spreading associated with electrical-only nerve stimulation stimulates many frequencies and therefore causes the perceived sense of sound for the person to be distorted compared to the sound in.

Figures 1, 1C, 2:
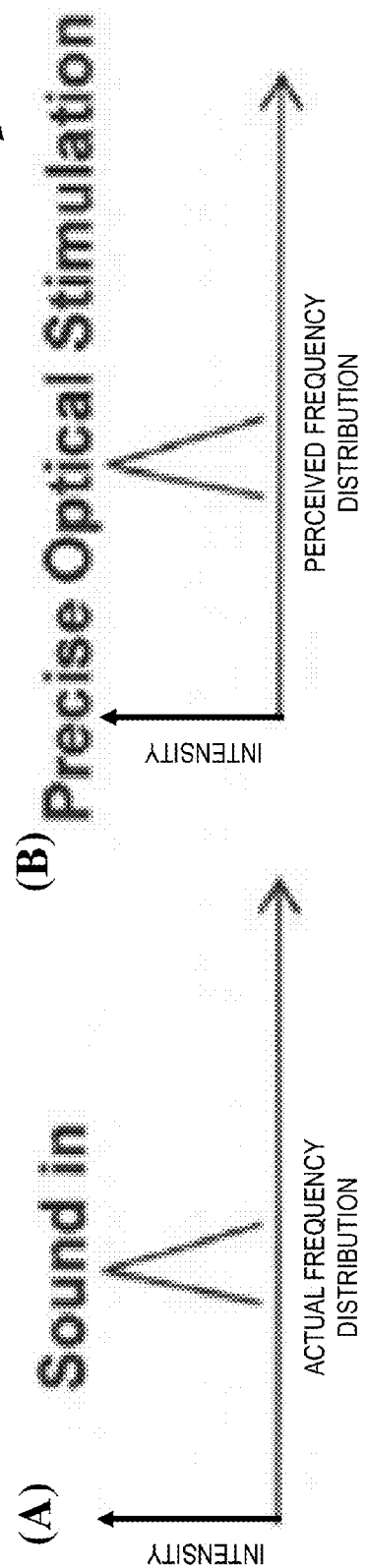

FIG. 1C-2 is a pair of graphs 103 illustrating the advantages of optical-based nerve stimulation of the cochlea. Graph (A) of FIG. 1C-2 is identical to Graph (A) of FIG. 1C-1. Graph (B) of FIG. 1C-2 shows the perceived sense of sound for a person created by an optical-based nerve stimulator that stimulates the cochlea of the person based on the sound signal of Graph (A) of FIG. 1C-2. As shown by Graph (B) of FIG. 1C-2, the precision of optical-based nerve stimulation more closely mimics the sound in, as compared to electrical-only stimulation.

FIG. 1D-1 is a pair of graphs 104 illustrating the limitations of electrical-only nerve stimulation of the vestibular system. Graph (A) of FIG. 1D-1 shows an X-Y-Z coordinate representation of the rotation of a person's head (here, the graph happens to show movement in only the X direction). Graph (B) of FIG. 1D-1 shows the perceived sense of head rotation for a person created by an electrical-only nerve stimulator that stimulates the vestibular system of the person based on the head rotation shown in Graph (A) of FIG. 1D-1. As shown by Graph (B) of FIG. 1D-1, the spreading associated with electrical-only nerve stimulation causes the perceived sense of head rotation for the person to be in more than just the X direction.

FIG. 1D-2 is a pair of graphs 105 illustrating the advantages of optical-based nerve stimulation of the vestibular system. Graph (A) of FIG. 1D-2 is identical to Graph (A) of FIG. 1D-1. Graph (B) of FIG. 1D-2 shows the perceived sense of head rotation for a person created by an optical-based nerve stimulator that stimulates the vestibular system of the person based on the head rotation of Graph (A) of FIG. 1D-2. As shown by Graph (B) of FIG. 1D-2, the precision of optical-based nerve stimulation more closely mimics the sense of balance (in this case, related to head rotation), as compared to electrical-only stimulation.

Figure 2A:
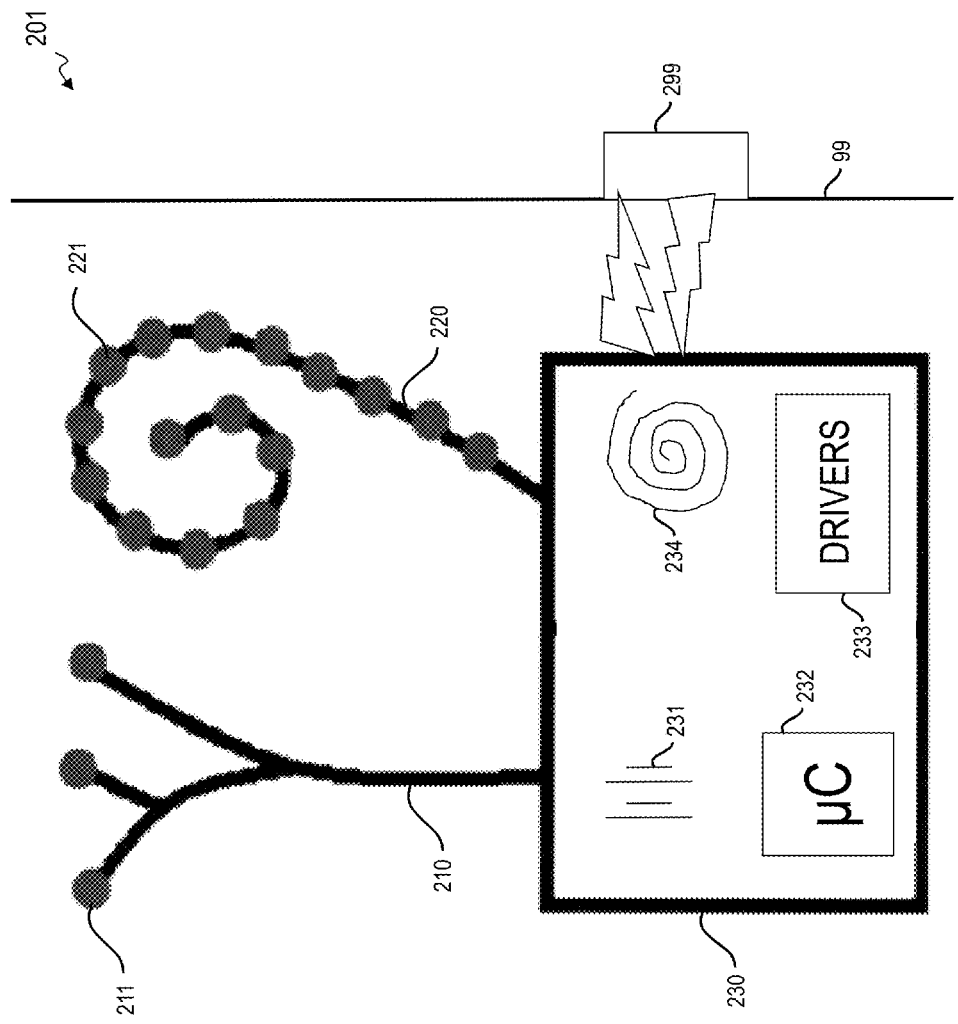
FIG. 2A is a schematic diagram of a vestibular-cochlear stimulation system 201.

FIG. 2A is a schematic diagram of a vestibular-cochlear stimulation system 201. In some embodiments, system 201 includes a vestibular-implant (VI) portion 210 and a cochlear-implant (CI) portion 220. In some embodiments, VI portion 210 includes a plurality of vestibular-stimulation sources 211. In some embodiments, stimulation sources 211 include a plurality of vertical-cavity-surface-emitting laser (VCSELs) and/or a plurality of electrodes. In some embodiments, CI portion 220 includes a plurality of cochlea-stimulation sources 221, and, in some such embodiments, stimulation sources 221 also include a plurality of VCSELs and a plurality of electrodes. In some embodiments, the VCSELs and the electrodes of stimulation sources 211 and 221 are configured to trigger nerve-action potentials (NAPs) in one or more nerve tissues. In some embodiments, VI portion 210 includes a vestibular-stimulation system such as described in U.S. Pat. No. 8,012,189, which is incorporated herein by reference in its entirety. In some embodiments, CI portion 220 includes a cochlear-stimulation system such as described in U.S. patent application Ser. No. 12/890,602, which is incorporated herein by reference in its entirety. In some embodiments, one or both of VI portion 210 and CI portion 220 includes one or more sensors (not shown) configured to detect the NAPs triggered by the stimulation signals delivered by stimulation sources 211 and provide feedback to controller 232 in order to more effectively stimulate the desired nerve tissues (e.g., in some embodiments, system 201 includes one or more audio-detection sensors (e.g., a microphone) configured to detect audio signals that are used by controller 232 to determine the appropriate control signals for controlling CI portion 220 to stimulate NAPs in cochlea 180, and system 201 includes one or more balance-detection sensors (e.g., a gyroscope, accelerometer, or the like) configured to detect balance information that is used by controller 232 to determine the appropriate control signals for controlling VI portion to stimulate NAPs in the vestibular system).

In some embodiments, system 201 includes a single device enclosure 230 that houses a single multi-function processor/controller 232 (e.g., a micro-controller) configured to control both VI portion 210 and CI portion 220, a power supply 231 configured to provide power for system 201, a radio-frequency transceiver 234, and drivers 233 operatively coupled to controller 232 (in some embodiments, drivers 233 include optical drivers to drive VCSELs and electrical drivers to drive electrodes). In some embodiments, enclosure 230 is placed inside the ear with VI portion 210 and CI portion 220. In some such embodiments, power supply 231 is a battery and is configured to be charged wirelessly (via transceiver 234) from an external device 299 located on the external surface 99 of the body. In some embodiments, external device 299 also includes one or more environment sensors configured to sense balance conditions and/or audio signals (associated with the person using system 201) and transmit controller-input signals based on the sensed data to controller 232. In some such embodiments, controller 232 processes the received controller-input signals and generates control signals for driving VI portion 210 and/or CI portion 220. In some embodiments, enclosure 230 is placed behind the ear lobe, external to the inner-ear labyrinth, and processor/controller 232 communicates with VI portion 210 and CI portion 220 through a wireless (e.g., via transceiver 234) or wired connection. In some such embodiments, enclosure 230 itself includes the one or more environment sensors.

In some embodiments, in order to lower the maximum instantaneous power required, controller 232 is configured to interleave pulses between CI portion 220 and VI portion 210 such that device doesn't have to send out more than one "pulse" (in some embodiments, an optical pulse, in some embodiments, an electrical pulse, or in some embodiments, a combined hybrid pulse) at a time.

Figure 2B:
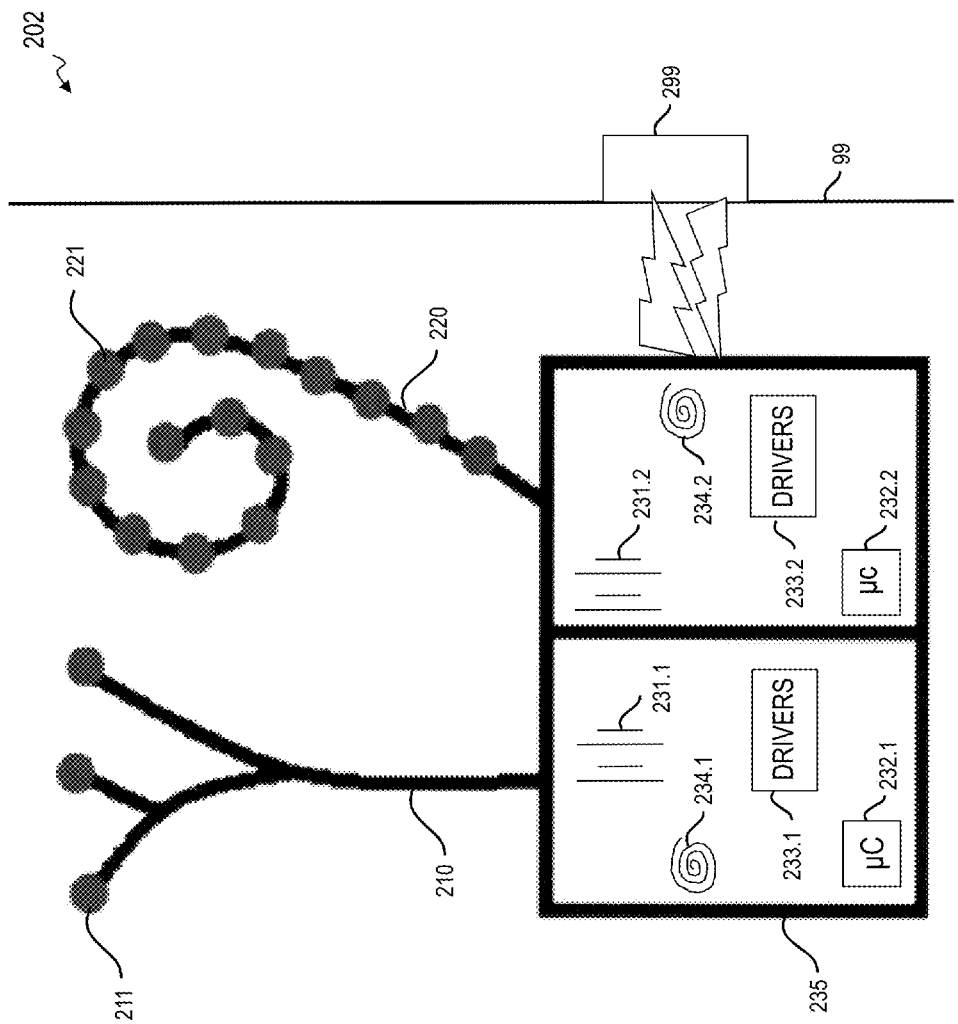
FIG. 2B is a schematic diagram of a vestibular-cochlear stimulation system 202.

FIG. 2B is a schematic diagram of a vestibular-cochlear stimulation system 202. In some embodiments, system 202 includes a single device enclosure 235 that is substantially similar to enclosure 230 except that VI portion 210 and CI portion 220 each have their own processor/controller, power supply, radio-frequency transceiver, and drivers. For example, in some embodiments, VI portion 210 includes a power supply 231.1, a transceiver 234.1, a controller 232.1, and drivers 233.1, and CI portion 220 includes a power supply 231.2, a transceiver 234.2, a controller 232.2, and drivers 233.2.

Figure 2C:
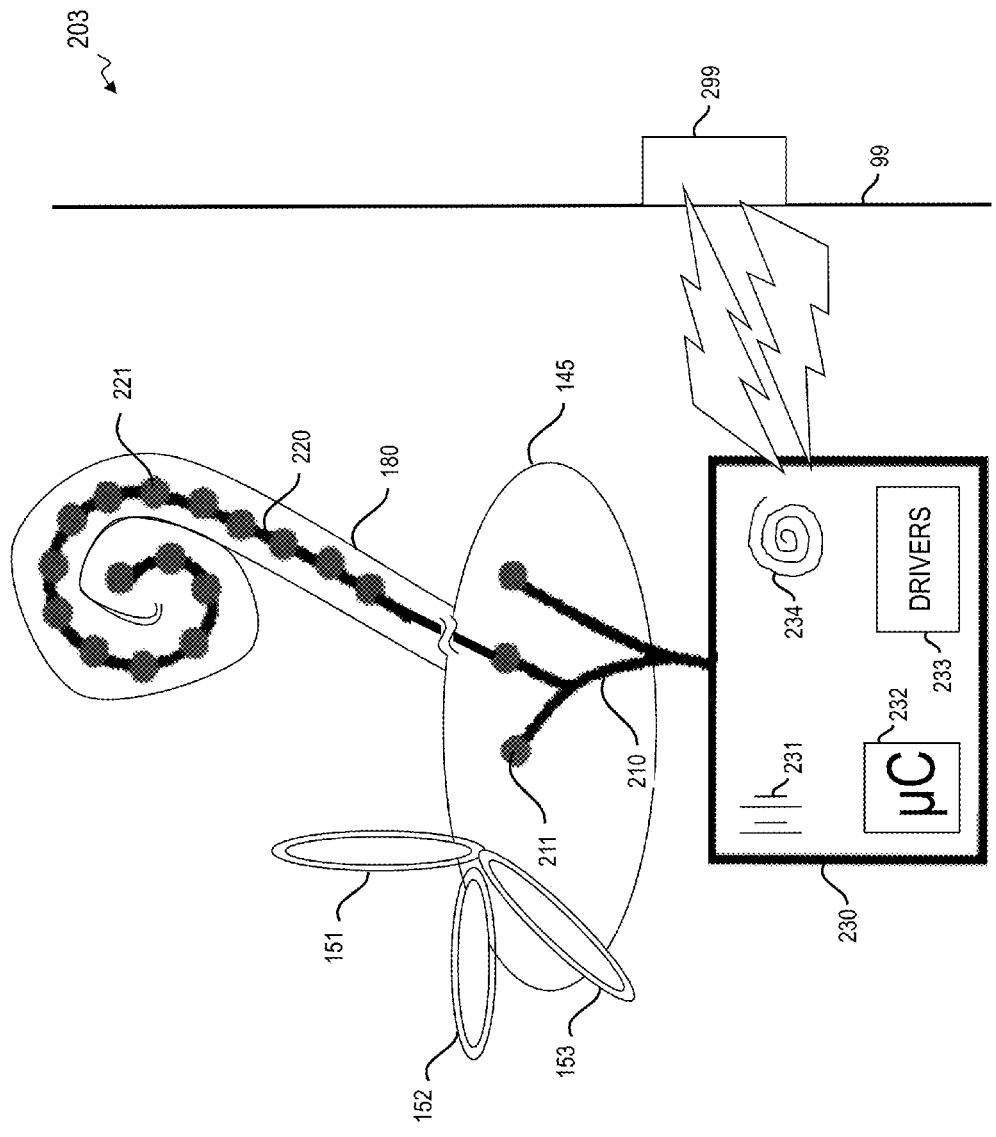
FIG. 2C is a schematic diagram of a vestibular-cochlear stimulation system 203.

FIG. 2C is a schematic diagram of a vestibular-cochlear stimulation system 203. In some embodiments, VI portion 210 and CI portion 220 are integrated together in one continuous implant such that CI portion 220 is operatively coupled directly to VI portion 210, which in turn is operatively coupled to controller 232. In some embodiments, CI portion 220 is inserted into cochlea 180 by passing CI portion 220 through vestibule 145 (in some embodiments, via an incision through oval window 146) and into the scala vestibuli of cochlea 180, and VI portion 210 (which is located between CI portion 220 and controller 232) is placed inside vestibule 145. Thus, in some embodiments, the single incision into the vestibule-cochlea organ is used for insertion of, and connection to, both the CI portion 220 and VI portion 210. In other embodiments, CI portion 220 is inserted into cochlea 180 via an incision through round window 181 and at least a portion of VI portion 210 is inserted into vestibule 145 via an incision through oval window 146. In still other embodiments, in addition to both CI portion 220 and VI portion 210 being inserted into the vestibule-cochlea organ via oval window 146, a secondary cochlear stimulator (not shown) is also inserted into cochlea 180, but the secondary cochlear stimulator is inserted into the scala tympani of cochlea 180 via round window 181.

Figure 2D:
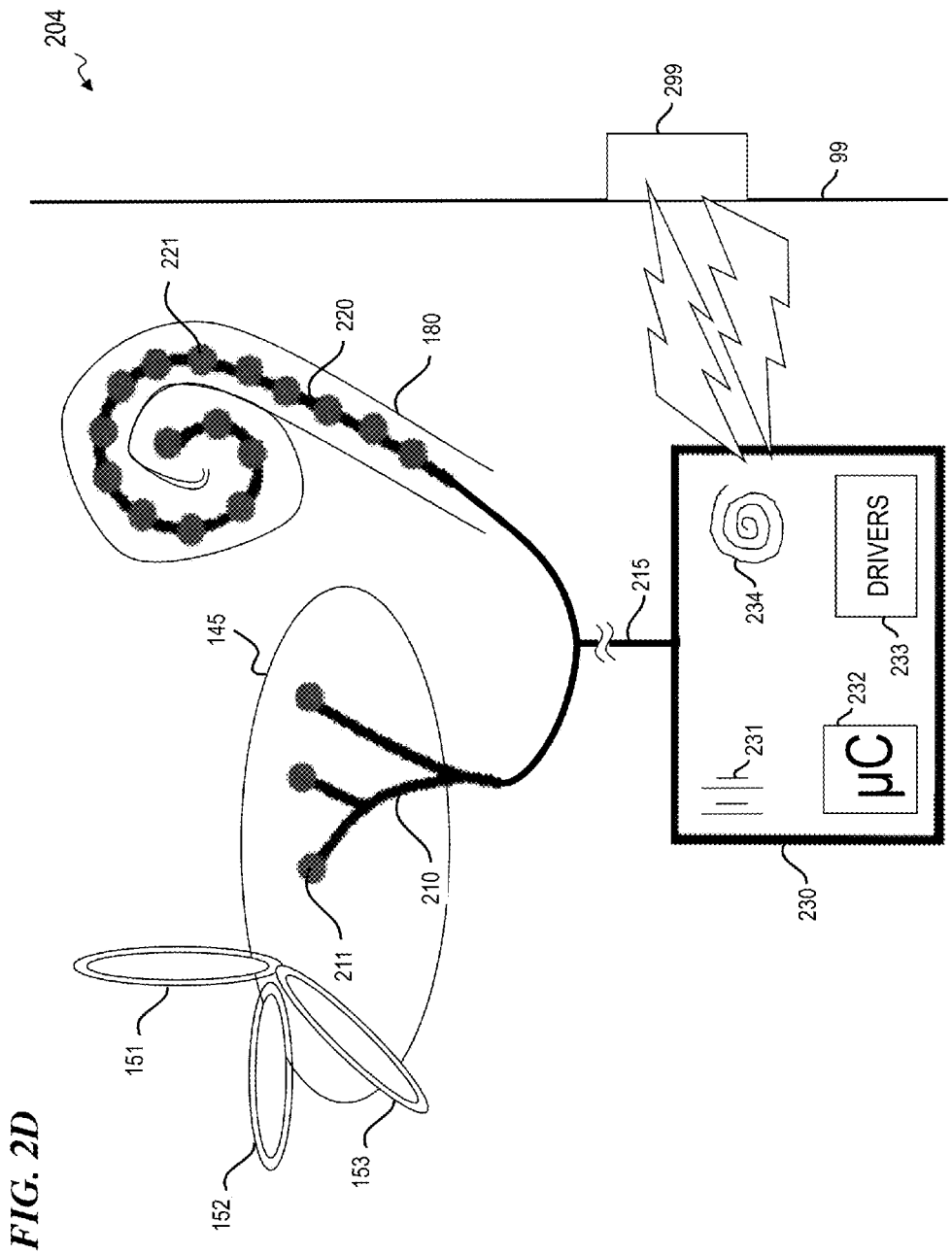
FIG. 2D is a schematic diagram of a vestibular-cochlear stimulation system 204.

FIG. 2D is a schematic diagram of a vestibular-cochlear stimulation system 204. In some embodiments, instead of being physically connected in series to each other such as shown in FIG. 2C, VI portion 210 and CI portion 220 share a common connection 215 (in some embodiments, a wired connection; in other embodiments, a wireless connection) to enclosure 230 and its components. In some such embodiments, CI portion 220 is inserted into cochlea 180 by passing CI portion 220 through round window 181 (e.g., in some embodiments, via an incision through round window 181) and into cochlea 180, and VI portion 210 is placed inside vestibule 145 via oval window 146 (e.g., in some embodiments, via an incision through oval window 146).

FIG. 3 is a table 301 showing the various combinations of inner-ear nerve stimulation that are possible with the combined VI portion 210 and CI portion 220 shown in FIGS. 2A-2D. In some embodiments, the inner-ear nerve stimulation described by FIG. 3 includes the triggering of nerve-action potentials (NAPs) in one or more nerve tissues of the target system (e.g., the cochlea). In some embodiments, for example, VI portion 210 and CI portion 220 are both used to provide infrared nerve stimulation (INS) to the vestibular and cochlear systems, respectively, of the inner ear.

In some embodiments, as a further example, VI portion 210 provides INS to the vestibular system while CI portion 220 provides a hybrid of INS and electrical stimulation to the cochlea. In some such embodiments, CI portion 220 includes a system such as described in U.S. patent application Ser. No. 13/555,091, which is incorporated herein by reference.

In some embodiments, as still another example, VI portion 210 provides nerve stimulation via an optogenetics-based procedure/system, while CI portion 220 provides nerve stimulation via INS. As used herein, optogenetics involves the introduction of fast light-activated channels and enzymes that allow temporally precise manipulation of electrical and biochemical events while maintaining cell-type resolution through the use of specific targeting mechanisms. In some embodiments, the optogenetics-based procedures provided by one or both of the VI portion 210 and the CI portion 220 includes procedures such as those described in Boyden et al. (U.S. Patent Application Publication 2007/0261127), which is incorporated herein by reference. In some embodiments, the optogenetics-based procedures provided by one or both of the VI portion 210 and the CI portion 220 includes procedures such as those described in Zhang et al. (U.S. Patent Application Publication 2009/0093403), which is incorporated herein by reference.

Figure 4A:
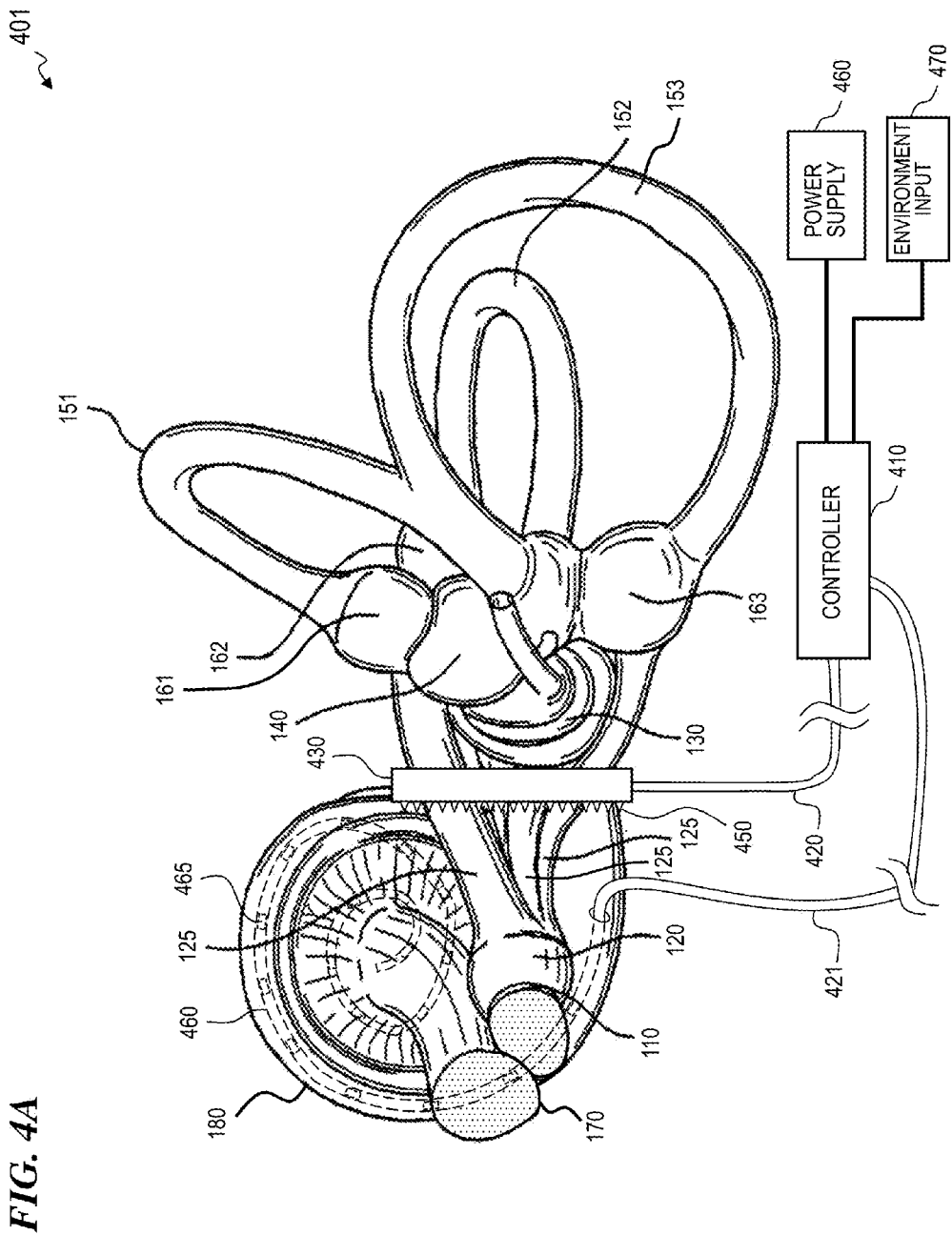
FIG. 4A is a perspective view of an inner-ear labyrinth and a vestibular-cochlear stimulation system 401 that uses a single controller 410.

FIG. 4A is a perspective view of an inner-ear labyrinth and a vestibular-cochlear stimulation system 401 that uses a single controller 410. In some embodiments, controller 410 is operatively connected to a VCSEL-array head 430 through an electrical bundle 420 and controller 410 provides a plurality of electrical signals to VCSEL-array head 430 in order to drive the VCSELs of head 430. In some embodiments (not shown) controller 410 includes a wireless transceiver configured to transmit and receive wireless signals such that controller 410 communicates with and controls VCSEL-array head 430 wirelessly.

In some embodiments, VCSEL-array head 430 is implanted near the vestibular organs and the electrical signals drive VCSEL-array head 430 such that it produces a plurality of laser light signals. In some embodiments, VCSEL-array head 430 contains a plurality of optical lenses 450 configured to direct the laser light on to the nerves and/or tissue. In the embodiment shown, optical lenses 450 direct the light signals from the VCSEL-array head 430 toward the vestibular nerve branches 125. In other embodiments, optical lenses 450 direct the light signals from the VCSEL-array head 430 toward the vestibular nerve 110. In still other embodiments, optical lenses 450 direct the light signals from VCSEL-array head 440 toward one or more nerves of the vestibular ampullae 161, 162, 163, utricle 140, and the saccule 130. In some embodiments, VCSEL-array head 430 does not include lenses 450 and is configured to direct the laser light toward vestibular nerve 110, vestibular ampullae 161, 162, 163, utricle 140, and/or saccule 130.

In some embodiments, long-wavelength VCSEL devices and/or VCSEL arrays, such as described in U.S. Pat. No. 7,031,363 and U.S. Pat. No. 7,004,645 (which are each incorporated herein by reference), are used for the VCSEL-array head 430 in FIG. 4A.

In some embodiments, VCSEL controller 410 is also operatively connected to a cochlear stimulator 460 that includes a plurality of optical and/or electrical stimulators 465. In some such embodiments, controller 410 is connected to stimulator 460 via an electrical bundle 421. In other embodiments (not shown), controller 410 includes a wireless transceiver configured to transmit and receive wireless signals such that controller 410 communicates with and controls stimulator 460 wirelessly. In some embodiments, cochlear stimulator 460 is at least partially inserted into the cochlea 180 (in some such embodiments, stimulator 460 is inserted into cochlea 180 via round window 181 of cochlea 180). In other embodiments, stimulator 460 is placed outside of the cochlea 180. In some embodiments, cochlear stimulator 460 includes a cochlear-stimulation system such as described in U.S. patent application Ser. No. 12/890,602, which is incorporated herein by reference in its entirety.

In some embodiments, controller 410 is operatively coupled to a power source 460 configured to provide power to operate controller 410, head 430, and stimulator 460. In some embodiments, controller 410 is also operatively coupled to an environment-input mechanism 470 configured to receive environment conditions (e.g., balance conditions and/or audio signals), generate controller-input signals based on the received environment conditions, and transmit the generated controller-input signals to controller 410. In some embodiments, controller 410 includes a processor configured to process the controller-input signals and generate appropriate control signals for the head 430 and/or stimulator 460 such that head 430 and/or stimulator 460 deliver stimulation signals that trigger NAPs in the desired nerve tissues.

Figure 4B:
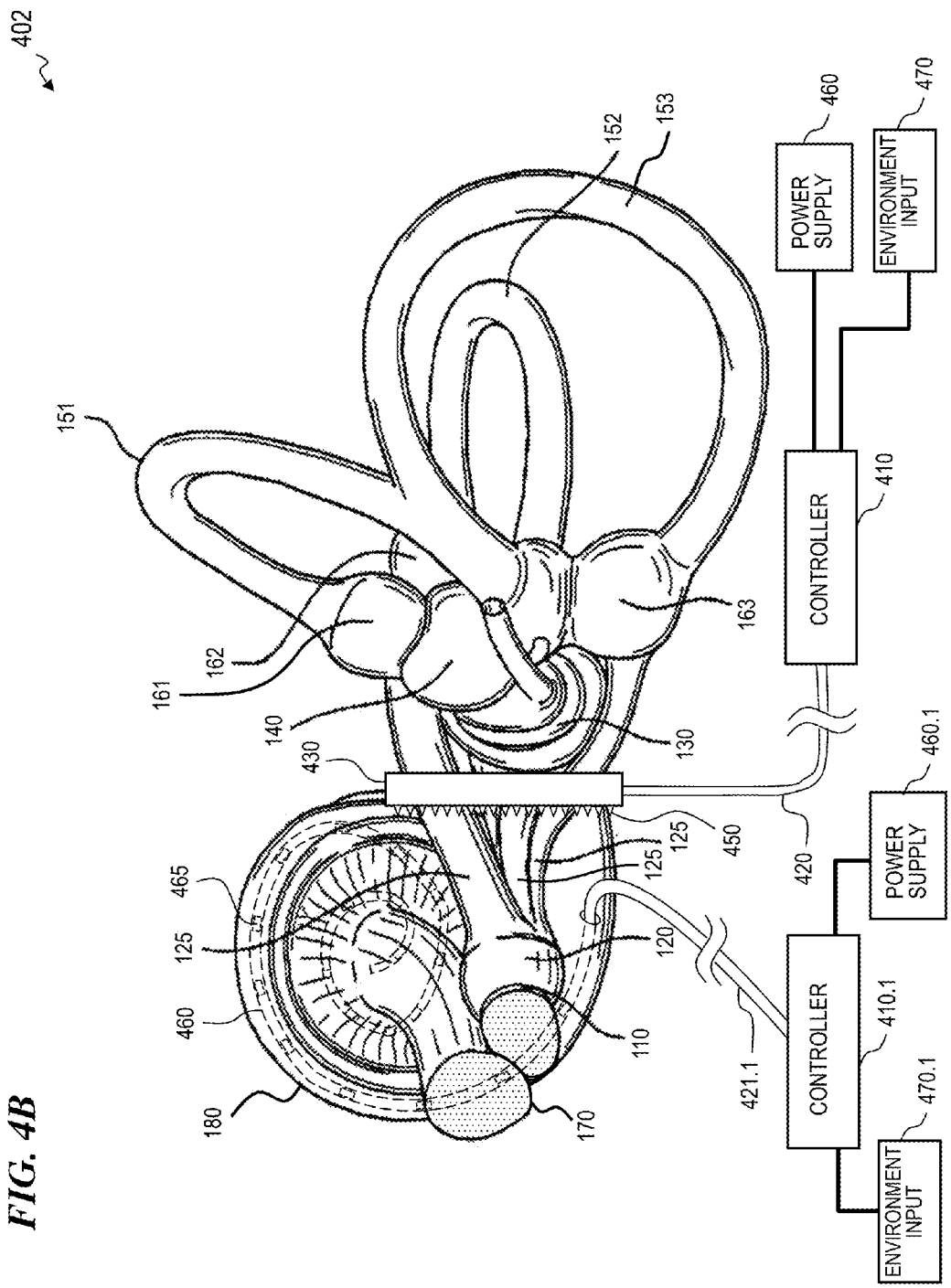
FIG. 4B is a perspective view of an inner-ear labyrinth and a vestibular-cochlear stimulation system 402 that uses multiple controllers.

FIG. 4B is a perspective view of an inner-ear labyrinth and a vestibular-cochlear stimulation system 402 that uses multiple controllers. In some embodiments, head 430 is controlled by a controller 410 and stimulator 460 is controlled by a controller 410.1. In some embodiments, both controller 410 and controller 410.1 are contained within a single device enclosure (in some embodiments, this enclosure is implanted within the inner-ear labyrinth while, in other embodiments, this enclosure is located behind the ear lobe). In some embodiments, controller 410.1 is connected to stimulator 460 via an electrical bundle 421.1. In other embodiments (not shown), controller 410.1 includes a wireless transceiver configured to transmit and receive wireless signals such that controller 410.1 communicates with and controls stimulator 460 wirelessly. In some embodiments, controller 410.1 is further coupled to its own environment-input mechanism 470.1 and to its own power supply 460.1.

Figure 5A:
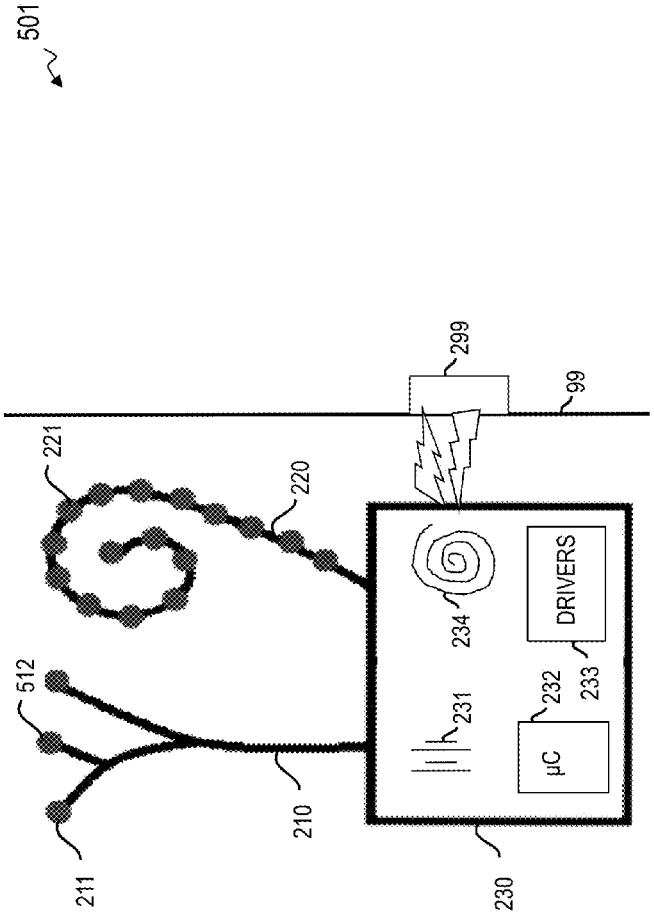
FIG. 5A is a schematic diagram of a vestibular-cochlear stimulation system 501.

FIG. 5A is a schematic diagram of a vestibular-cochlear stimulation system 501. The vestibular system has a background, spontaneous nerve firing rate of about 100 Hz, and the vestibular system encodes balance information by modulating the background rate up (to approximately 400 Hz) or down (to approximately zero). In a typical prosthesis, there is no way to lower the background firing rate of the vestibular system. Therefore, in some embodiments, in addition to being configured to trigger NAPs in nerve tissue of the vestibular system, system 501 is also configured to inhibit NAPs triggered as part of the background nerve firing rate associated with the vestibular system. For example, in some embodiments, system 501 includes one or more sensors 512 configured to sense the background firing rate of the vestibular system, generate background-rate signals based on the sensed rate, and transmit the background-rate signals to controller 232. In some such embodiments, controller 232 processes the received background-rate signals and automatically controls system 501 to deliver the stimulation or inhibition signals necessary to provide an appropriate balance sensation to the person using system 501 (in some embodiments, controller 232 also receives sense-of-balance controller-input signals from one or more sensors operatively coupled to controller 232 (e.g., in some embodiments, sensors located in external device 299 that communicate wirelessly with controller 232 via transceiver 234) in order to determine the appropriate balance sensation for the person).

In some embodiments, stimulators 211 include a plurality of VCSELs and system 501 provides both inhibition and stimulation via the plurality of VCSELs by changing the optical parameters of the signals delivered by the plurality of VCSELs (e.g., pulse width, repetition rate, energy, or the like). In some embodiments, stimulators 211 include a combination of VCSELs and electrodes and inhibition is provided by the plurality of VCSELs while NAPs are triggered by electrical stimulation or by an optogenetics-based procedure. In some embodiments, system 501 includes a nerve-inhibition system such as those described in U.S. Patent Application Publication 2013/0013030, which is incorporated herein by reference.

Figure 5B:
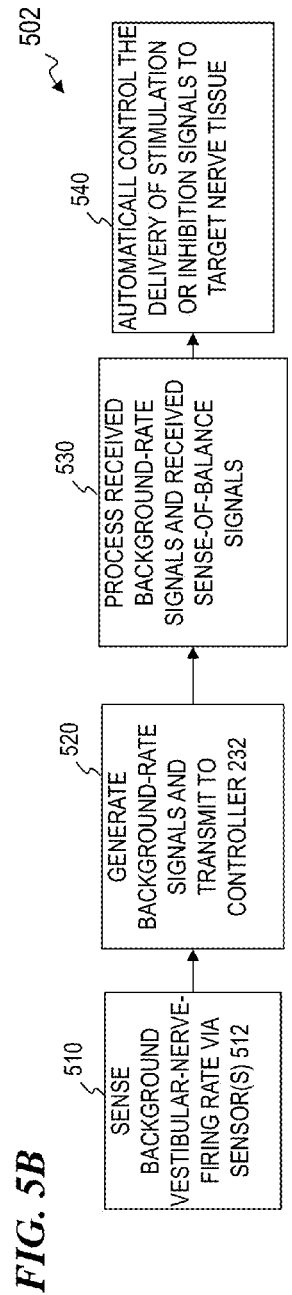
FIG. 5B is a block diagram of a method for stimulating the vestibular system of a person using system 501.

FIG. 5B is a block diagram of a method for stimulating the vestibular system of a person using system 501. In some embodiments, at block 510, one or more sensors 512 sense the background vestibular-nerve-firing rate. In some embodiments, at block 520, sensors 512 generate background-rate signals based on the sensed background vestibular-nerve-firing rate and transmit the generated background-rate signals to controller 232. In some embodiments, at block 530, controller 232 processes the received background-rate signals and any received sense-of-balance signals. In some embodiments, at block 540, controller 232 automatically controls the delivery of stimulation or inhibition signals to the target nerve tissue in order to provide an appropriate sense of balance to the person using system 501.

Figure 6:
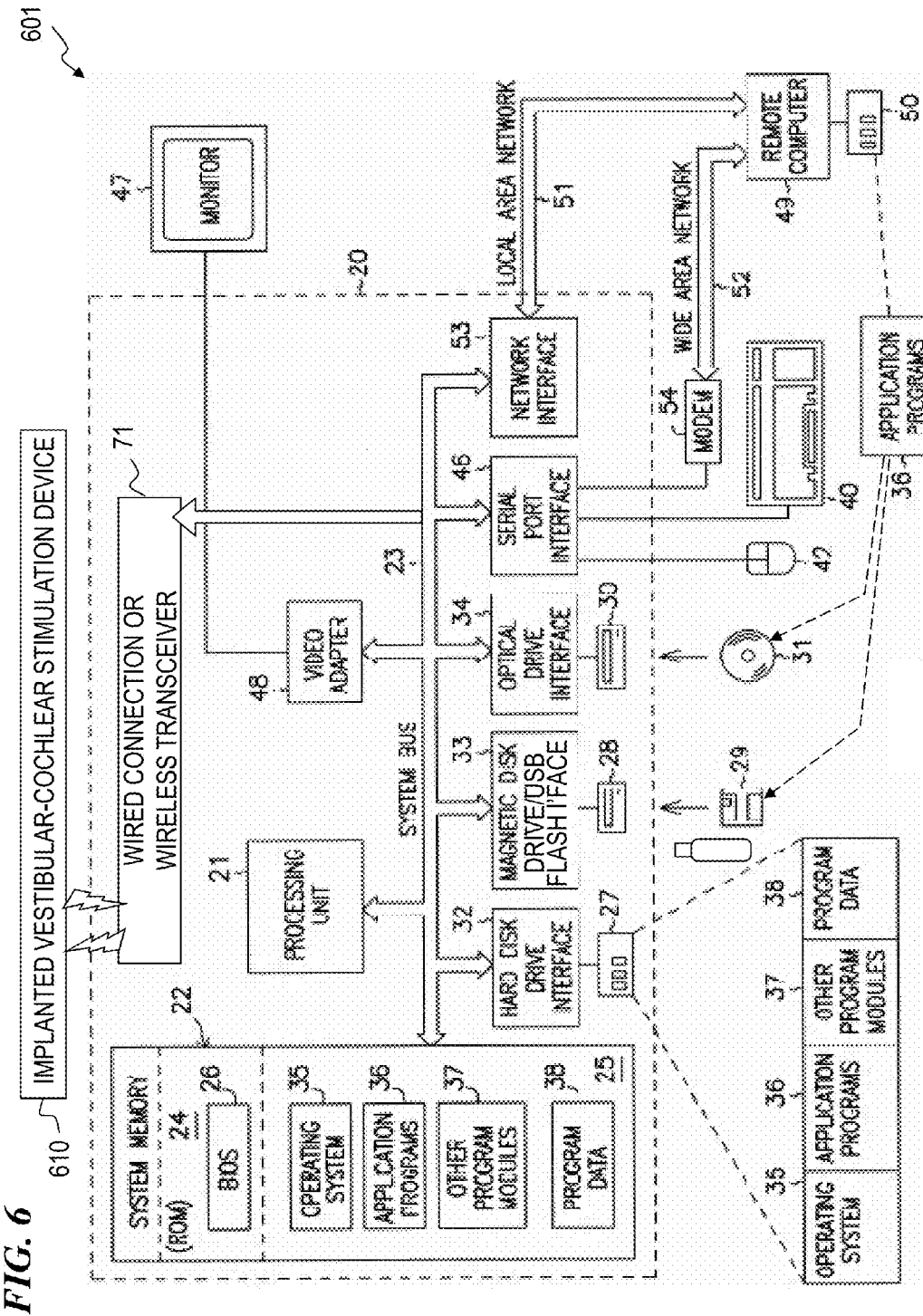
FIG. 6 is an overview diagram of a hardware- and operating-environment (or system) 601 that is used in conjunction with embodiments of the invention.

FIG. 6 is an overview diagram of a hardware- and operating-environment (or system) 601 that is used in conjunction with embodiments of the invention. The description of FIG. 6 is intended to provide a brief, general description of suitable computer hardware and a suitable computing environment in conjunction with which the invention may be implemented. In some embodiments, the invention is described in the general context of computer-executable instructions (e.g., in some embodiments, these instructions are stored on non-transient storage media such as USB FLASH drives, floppy disks, CDROM, storage connected to the internet, or the like, and are used for performing a method used in some embodiments of the present invention), such as program modules, that are stored on computer-readable media and that are executed by a computer system 601, such as a microprocessor residing in an implanted device 610 (located within a patient) and/or in an external device worn by the patient and/or personal computer that is/are wirelessly linked to the implanted device 610 (e.g., external device 299 of FIG. 2A). Generally, program modules include routines, programs, objects, components, data structures, and the like, that perform particular tasks or implement particular abstract data types.

In some embodiments, system 601 includes an audiologist-, surgeon- and/or user-control console computer 20 that is programmable and that has a wireless (or wired, optical fiber, or other direct connection) transceiver 71 that allows wireless control of, and/or sensing from (i.e., reprogramming of the remote microprocessors, as well as receiving sensed signals and diagnostic information from), the implanted vestibular-cochlear stimulation device 610 (which, in some embodiments, includes a programmed microcontroller such as controller 232 of FIG. 2A). In some embodiments, system 601 controls the triggering of nerve-action potentials (NAPs) in the nerves of the cochlea and/or vestibular system (for example, in some embodiments, system 601 controls the delivery of optical-stimulation signals (e.g., INS signals) that trigger an electrical response in one cochlear nerve or a small subset of cochlear nerves, and that response is detected using one or more electrodes in device 610 and then used (optionally along with reported feedback from the patient) to determine whether the device successfully triggered the desired NAPs and thus the desired sense of hearing).

In some embodiments, computer instructions are stored in application programs 36 and/or other program modules 37 that are stored and accessed from a storage device such as a hard disk 27, a magnetic floppy disk or USB (universal-serial bus) FLASH device 29 (often called a "thumb drive") that is read and/or written by interface unit 28, an optical disk 31 that is read and/or written by optical disk drive 30, or from a remote computer 49 having storage device 50 accessed across a local area network (LAN) 51 or a wide-area network (WAN) 52 such as the internet. Thus, some embodiments provide such non-transitory storage media (29, 31, and/or 50) for storing instructions that, when executed in computer 20, and/or in device 610, perform the methods of the present invention. In some embodiments, these methods include the output-signal drive and input-signal sensing functions for the nerve stimulation of the vestibular system and/or cochlea, including the various combinations of INS, electrical, and/or optogenetics-based nerve stimulation, and the combination of the triggering of NAPs and the inhibition of NAPs in the vestibular nerve tissue. Note that in some embodiments, a plurality of the optical-signal-based diagnostic sensing and feedback functions are implemented within a single device 610.

In some embodiments, console computer 20 communicates bi-directionally with, and/or provides power to, the device 610. In some embodiments, application programs 36 stored on a computer-readable storage device (e.g., optical disk 31 (CDROM, DVD, blue-ray disk (BD), or the like), magnetic or FLASH storage device 29 (e.g., floppy disk, thumb drive, SDHC memory card or the like), and/or a storage device 50 connected to a remote computer 49 that connects to computer 20 across a local-area network 51 or a wide-area network 52 such as the internet) contain instructions and/or control structures (such as look-up tables, control parameters, databases and the like) that are processed and/or transmitted into the implanted device 610 to control its operation by methods of the present invention described herein. In some embodiments, the applications programs 36 are partially executed in the computer 20 and/or an externally worn device (e.g., external device 299 of FIG. 2A), and then partially executed in the implanted device 610.

In some embodiments, the present invention provides a method for triggering nerve-action potentials (NAPs) in each one of a plurality of cochlear neurons in a cochlea of a person and in each one of a plurality of vestibular neurons in a vestibular organ of the person in order to provide auditory and balance sensations for the person, the method including generating a first plurality of light signals that, when applied to a selected one of the plurality of cochlear neurons, stimulate a NAP in the selected cochlear neuron; delivering the first plurality of light signals to the selected cochlear neuron from within the cochlea; generating a second plurality of light signals that, when applied to a selected one of the plurality of vestibular neurons, stimulate a NAP in the selected vestibular neuron; delivering, during a first period of time, the second plurality of light signals to the selected vestibular neuron from within the vestibular organ; and selectively controlling the first plurality and the second plurality of light signals to optically stimulate the selected cochlear neuron and the selected vestibular neuron in order to trigger NAPs of the selected cochlear neuron and the selected vestibular neuron.

In some embodiments, the method further includes receiving an audio signal; receiving an orientation signal; processing the received audio signal and generating cochlear-pulse-repetition-rate information and cochlear-pulse-intensity information based on the received audio signal, wherein the selectively controlling of the first plurality of light signals includes selectively controlling the first plurality of light signals to emit light pulses to selected locations of the cochlea based on the cochlear-pulse-repetition-rate information and the cochlear-pulse-intensity information; and processing the received orientation signal and generating vestibular-pulse-repetition-rate information and vestibular-pulse-intensity information based on the received orientation signal, wherein the selectively controlling of the second plurality of light signals includes selectively controlling the second plurality of light signals to emit light pulses to selected locations of the vestibular organ based on the vestibular-pulse-repetition-rate information and the vestibular-pulse-intensity information.

In some embodiments, the method further includes generating a third plurality of light signals that, when applied to the selected vestibular neuron of the person, reduces a background-NAP rate in the selected vestibular neuron; delivering, during a second period of time, the third plurality of light signals to the selected vestibular neuron; and selectively controlling the third plurality of light signals to reduce the background-NAP rate of the selected vestibular neuron during the second period of time.

In some embodiments, the method further includes detecting a background-NAP rate associated with the selected vestibular neuron; generating a third plurality of light signals that, when applied to the selected vestibular neuron of the person, reduces the background-NAP rate in the selected vestibular neuron; delivering, during a second period of time, the third plurality of light signals to the selected vestibular neuron; and selectively controlling the third plurality of light signals to reduce the background-NAP rate of the selected vestibular neuron during the second period of time.

In some embodiments, the method further includes generating a first plurality of electrical-stimulation signals that, when applied to the plurality of cochlear neurons, sensitize the plurality of cochlear neurons; delivering the first plurality of electrical-stimulation signals to the plurality of cochlear neurons including the selected cochlear neuron; generating a second plurality of electrical-stimulation signals that, when applied to the plurality of vestibular neurons, sensitize the plurality of vestibular neurons; delivering the second plurality of electrical-stimulation signals to the plurality of vestibular neurons including the selected vestibular neuron; and selectively controlling the first and second plurality of electrical-stimulation signals to sensitize the plurality of cochlear neurons and the plurality of vestibular neurons in order to control NAPs of the selected cochlear neuron and the selected vestibular neuron, but wherein others of the plurality of sensitized cochlear and vestibular neurons are not optically stimulated such that NAPs are not triggered in those other sensitized cochlear and vestibular neurons.

In some embodiments, the method further includes optogenetically modifying the selected cochlear neuron and the selected vestibular neuron; and using wavelengths selected for the optogenetically modified cochlear neuron and vestibular neuron, triggering NAPs in the cochlear neuron and the vestibular neuron.

In some embodiments of the method, the delivering of the first plurality of light signals to the selected cochlear neuron includes generating infrared light from a plurality of vertical-cavity-surface-emitting lasers (VCSELs).

In some embodiments, the present invention provides an apparatus for stimulating nerve-action potentials (NAPs) in each one of a plurality of cochlear neurons in a cochlea of a person and in each one of a plurality of vestibular neurons in a vestibular organ of the person in order to provide auditory and balance sensations for the person, the apparatus including a cochlear-implant portion, wherein the cochlear-implant portion includes a first plurality of independently controllable light sources that are configured to generate a first plurality of light signals, including a first light signal and a second light signal, that, when applied to a selected one of the plurality of cochlear neurons, each stimulate a nerve action potential (NAP) in the selected cochlear neuron, and a first transmission medium configured to transmit the first plurality of light signals from the first plurality of light sources to the selected cochlear neuron in order to trigger NAPs in the selected cochlear neuron; a vestibular-implant portion, wherein the vestibular-implant portion includes a second plurality of independently controllable light sources that are configured to generate a second plurality of light signals, including a third light signal and a fourth light signal, that, when applied to a selected one of the plurality of vestibular neurons of a vestibular system of the person, each stimulate a nerve action potential (NAP) in the selected vestibular neuron, and a second transmission medium configured to transmit the second plurality of light signals from the second plurality of light sources to the selected vestibular neuron in order to trigger NAPs in the selected vestibular neuron; and a controller operatively coupled to the cochlear-implant portion to selectively control the first plurality of light signals from each of the first plurality of light sources such that the first plurality of light signals provide controlled optical stimulation to the selected cochlear neuron in order to trigger nerve action potentials (NAPs) produced by the selected cochlear neuron, and wherein the controller is also operatively coupled to the vestibular-implant portion to selectively control the second plurality of light signals from each of the second plurality of light sources such that the second plurality of light signals provide controlled optical stimulation to the selected vestibular neuron in order to trigger nerve action potentials (NAPs) produced by the selected vestibular neuron.

In some embodiments, the apparatus further includes an audio-signal sensor configured to receive an audio signal and transmit an audio-controller-input signal to the controller based on the received audio signal; and an orientation-signal sensor configured to receive an orientation signal and transmit an orientation-controller-input signal to the controller based on the received orientation signal, wherein the controller is further configured to receive the audio-controller-input signal and the orientation-controller-input signal to obtain audio information and orientation information, wherein the controller is further configured to control the first plurality of light signals to emit light pulses to selected locations of the cochlea based on the audio information, and wherein the controller is further configured to control the second plurality of light signals to emit light pulses to selected locations of the vestibular organ based on the balance information.

In some embodiments of the apparatus, the second plurality of light sources is configured to generate a third plurality of light signals that, when applied to the selected vestibular neuron of the person, reduces a background-NAP rate in the selected vestibular neuron; wherein the second transmission medium is further configured to deliver the third plurality of light signals to the selected vestibular neuron during a second period of time; and wherein the controller is further configured to selectively control the third plurality of light signals to reduce the background-NAP rate of the selected vestibular neuron during the second period of time.

In some embodiments, the apparatus further includes a background sensor configured to detect a background-NAP rate associated with the selected vestibular neuron and transmit a background-NAP-rate signal to the controller, wherein the controller is further configured to process the received background-NAP-rate signal to obtain the background-NAP rate, and wherein the controller is further configured to control the third plurality of light signals to reduce the background-NAP rate of the selected vestibular neuron during the second time period based on the received background-NAP-rate signal.

In some embodiments, the apparatus further includes a first plurality of electrodes configured to generate a first plurality of electrical signals that, when applied to the plurality of cochlear neurons including the selected cochlear neuron, sensitize the plurality of cochlear neurons; a third transmission medium configured to deliver the first plurality of electrical signals to the plurality of cochlear neurons; a second plurality of electrodes configured to generate a second plurality of electrical signals that, when applied to the plurality of vestibular neurons including the selected vestibular neuron, sensitize the plurality of vestibular neurons; a fourth transmission medium configured to deliver the second plurality of light signals to the plurality of vestibular neurons, wherein the controller is further configured to selectively control the first and second plurality of electrical signals to sensitize the plurality of cochlear neurons and the plurality of vestibular neurons in order to control NAPs of the selected cochlear neuron and the selected vestibular neuron, but wherein others of the plurality of sensitized cochlear and vestibular neurons are not optically stimulated such that NAPs are not triggered in those other sensitized cochlear and vestibular neurons.

In some embodiments of the apparatus, the first plurality of independently controllable light sources includes a plurality of vertical-cavity surface-emitting lasers (VCSELs). In some embodiments, the controller is further configured to selectively change a wavelength of the first and second plurality of light signals to be a selected one of a plurality of selectable wavelengths. In some embodiments, the controller is further configured to selectively control a duty cycle of the first and second plurality of light signals. In some embodiments, the first transmission medium includes a plurality of optical fibers, each having a conductive material applied to a surface of the optical fiber. In some embodiments, the first transmission medium includes a lens and an optical fiber optically coupled to the lens. In some embodiments, the first transmission medium includes a plurality of parallel optical-signal-transmission waveguides.

In some embodiments of the apparatus, the first transmission medium is further configured to transmit a first pulsed light signal at a first time, wherein the second transmission medium is further configured to transmit a second pulsed light signal at a second time, and wherein the controller is further configured to interleave the transmission of the pulsed light signals generated by the first plurality of light sources and the second plurality of light sources, wherein the first time is different than the second time.

In some embodiments, the present invention provides an apparatus that includes means for generating a first plurality of light signals that, when applied to a selected one of the plurality of cochlear neurons, stimulate a NAP in the selected cochlear neuron; means for delivering the first plurality of light signals to the selected cochlear neuron from within the cochlea; means for generating a second plurality of light signals that, when applied to a selected one of the plurality of vestibular neurons, stimulate a NAP in the selected vestibular neuron; means for delivering, during a first period of time, the second plurality of light signals to the selected vestibular neuron from within the vestibular organ; and means for selectively controlling the first plurality and the second plurality of light signals to optically stimulate the selected cochlear neuron and the selected vestibular neuron in order to trigger NAPs of the selected cochlear neuron and the selected vestibular neuron.

In some embodiments, the present invention provides a method for triggering of nerve-action potentials (NAPs) in one or more neurons in a cochlea of a person and in one or more neurons of a vestibular system of the person in order to provide auditory and balance sensations for the person, the method including generating a first plurality of light signals that, when applied to a cochlear neuron of the person, stimulate a NAP in the cochlear neuron; delivering the first plurality of light signals to one or more cochlear neurons of the person; generating a second plurality of light signals that, when applied to a vestibular neuron of the person, stimulate a NAP in the vestibular neuron; delivering the second plurality of light signals to one or more vestibular neurons of the person; and selectively controlling the first and second plurality of light signals to optically stimulate the one or more cochlear and vestibular neurons in order to control NAPs produced by the one or more cochlear neurons and the one or more vestibular neurons.

In some embodiments, the method further includes receiving an audio signal; receiving a orientation/balance signal (e.g., a signal indicative of an orientation or a balance parameter of the person); processing the received audio signal and the received balance signal to obtain frequency and intensity information, wherein the selectively controlling of the first and second plurality of light signals includes selectively controlling the first plurality of light signals to emit light pulses to selected locations of the cochlea based on the frequency information and at selected pulse-repetition rates based on the intensity information and selectively controlling the second plurality of light signals to emit light pulses to selected locations of the vestibular system based on the frequency information and at selected pulse-repetition rates based on the intensity information.

In some embodiments, the method further includes generating a third plurality of light signals that, when applied to a vestibular neuron of the person, inhibits a background-NAP rate in the vestibular neuron; delivering the third plurality of light signals to one or more vestibular neurons of the person; and selectively controlling the third plurality of light signals to inhibit the background-NAP rate of the one or more vestibular neurons in order to control NAPs produced by the one or more vestibular neurons.

In some embodiments, the method further includes detecting a background-NAP rate associated with the one or more vestibular neurons, wherein the selectively controlling of the third plurality of light signals includes selectively controlling the third plurality of light signals to inhibit the detected background-NAP rate.

In some embodiments, the method further includes generating a first plurality of electrical signals that, when applied to a cochlear neuron of the person, sensitize the cochlear neuron; delivering the first plurality of electrical signals to one or more cochlear neurons of the person; generating a second plurality of electrical signals that, when applied to a vestibular neuron of the person, sensitize the vestibular neuron; delivering the second plurality of light signals to one or more vestibular neurons of the person; and selectively controlling the first and second plurality of electrical signals to sensitize the one or more cochlear and vestibular neurons in order to control NAPs produced by the one or more cochlear and vestibular neurons.

In some embodiments, the method further includes optogenetically triggering NAPs in one or more cochlear and vestibular neurons. In some embodiments of the method, the delivering of the first plurality of light signals to one or more cochlear neurons of the person includes delivering infrared light from one or more vertical-cavity-surface-emitting lasers (VCSELs).

In some embodiments, the present invention provides an apparatus for stimulating nerve-action potentials (NAPs) in a cochlea and a vestibular system of a person, the apparatus including a cochlear-implant portion, wherein the cochlear-implant portion includes a first plurality of independently controllable light sources that are configured to generate a first plurality of light signals, including a first light signal and a second light signal, that, when applied to a cochlear neuron of the person, each stimulate a nerve action potential (NAP) in the cochlear neuron, and a first transmission medium configured to transmit the first plurality of light signals from the first plurality of light sources to one or more neurons in the cochlea in order to trigger NAPs in the one or more neurons of the cochlea; a vestibular-implant portion, wherein the vestibular-implant portion includes a second plurality of independently controllable light sources that are configured to generate a second plurality of light signals, including a third light signal and a fourth light signal, that, when applied to a vestibular neuron of a vestibular system of the person, each stimulate a nerve action potential (NAP) in the vestibular neuron, and a second transmission medium configured to transmit the second plurality of light signals from the second plurality of light sources to one or more neurons in the vestibular system in order to trigger NAPs in the one or more neurons of the vestibular system; and a controller operatively coupled to the cochlear-implant portion to selectively control the first plurality of light signals from each of the first plurality of light sources such that the first plurality of light signals provide controlled optical stimulation to the one or more of neurons of the cochlea in order to control nerve action potentials (NAPs) produced by the one or more neurons of the cochlea, and operatively coupled to the vestibular-implant portion to selectively control the second plurality of light signals from each of the second plurality of light sources such that the second plurality of light signals provide controlled optical stimulation to the one or more of neurons of the vestibular system in order to control nerve action potentials (NAPs) produced by the one or more neurons of the vestibular system.

In some embodiments, the controller includes both an audio-stimulation controller and a balance-stimulation controller. In some embodiments, the audio-stimulation controller and the balance-stimulation controller are housed in a single implanted enclosure. In other embodiments, the audio-stimulation controller and the balance-stimulation controller are each housed in their own separate implanted enclosures.

In some embodiments, the apparatus further includes an audio-signal sensor configured to receive an audio signal and transmit an audio-controller-input signal to the controller based on the received audio signal; and a balance-signal sensor configured to receive a balance signal and transmit a balance-controller-input signal to the controller based on the received balance signal, wherein the controller is further configured to receive the audio-controller-input signal and the balance-controller-input signal to obtain audio information and balance information, wherein the controller is further configured to control the first plurality of light signals to emit light pulses to selected locations of the cochlea based on the audio information, and wherein the controller is further configured to control the second plurality of light signals to emit light pulses to selected locations of the vestibular system based on the balance information.

In some embodiments of the apparatus, the second plurality of light sources is configured to generate a third plurality of light signals that, when applied to a vestibular neuron of the person, inhibits a background-NAP rate in the vestibular neuron; wherein the second transmission medium is further configured to deliver the third plurality of light signals to one or more vestibular neurons of the person; and wherein the controller is further configured to selectively control the third plurality of light signals to inhibit the background-NAP rate of the one or more vestibular neurons in order to control NAPs produced by the one or more vestibular neurons.

In some embodiments, the apparatus further includes a background sensor configured to detect a background-NAP rate associated with the one or more vestibular neurons and transmit a background-NAP-rate signal to the controller based on the detected background-NAP rate, wherein the controller is further configured to process the received background-NAP-rate signal to obtain the background-NAP rate, and wherein the controller is further configured to control the third plurality of light signals to inhibit the background-NAP rate of the one or more vestibular neurons based on the received background-NAP-rate signal.

In some embodiments, the apparatus further includes a first plurality of electrodes configured to generate a first plurality of electrical signals that, when applied to a cochlear neuron of the person, sensitize the cochlear neuron; a third transmission medium configured to deliver the first plurality of electrical signals to one or more cochlear neurons of the person; a second plurality of electrodes configured to generate a second plurality of electrical signals that, when applied to a vestibular neuron of the person, sensitize the vestibular neuron; a fourth transmission medium configured to deliver the second plurality of light signals to one or more vestibular neurons of the person, wherein the controller is further configured to selectively control the first and second plurality of electrical signals to sensitize the one or more cochlear and vestibular neurons in order to control NAPs produced by the one or more cochlear and vestibular neurons.

In some embodiments of the apparatus, the first plurality of independently controllable light sources includes a plurality of vertical-cavity surface-emitting lasers (VCSELs). In some embodiments, the controller is further configured to selectively control a wavelength of the first and second plurality of light signals. In some embodiments, the controller is further configured to selectively control a duty cycle of the first and second plurality of light signals. In some embodiments, the first transmission medium includes a plurality of optical fibers, each having a conductive material applied to a surface of the optical fiber. In some embodiments, the first transmission medium includes a lens. In some embodiments, the first transmission medium includes a plurality of parallel optical-signal-transmission channels. In some embodiments, the first and second plurality of light signals are pulsed light signals. In some embodiments, the first transmission medium is further configured to transmit a first pulsed light signal at a first time, wherein the second transmission medium is further configured to transmit a second pulsed light signal at a second time, and wherein the controller is further configured to interleave the transmission of the pulsed light signals generated by the first plurality of light sources and the second plurality of light sources such that the first time is different than the second time.

In some embodiments, the present invention provides a method for stimulating triggering of NAPs in neurons in the cochlea, in the cochlear nerve, and/or nerves of vestibular system to provide sensations (e.g., auditory and/or balance sensations) for the patient. This method includes generating a plurality of light signals that, when applied to a neuron of a person, can stimulate a nerve action potential in the neuron; delivering a first portion of the plurality of light signals to one or a plurality of neurons of the cochlea; delivering a second portion of the plurality of light signals to one or a plurality of neurons of the vestibular system; and selectively controlling the plurality of light signals to optically stimulate the one or more neurons in order to control nerve action potentials (NAPs) produced by the plurality of neurons. Some embodiments further include receiving (or measuring or sensing or obtaining) an environment signal (e.g., an audio signal or a balance signal); and processing the received environment signal to obtain frequency and intensity information, wherein the delivering of light signals comprises delivering the light pulses to neurons of the cochlea and/or the vestibular system, and wherein the selectively controlling of the light signals includes selectively controlling the light signals to emit light pulses to selected locations of the cochlea and/or the vestibular system of the patient based on the frequency information and at selected pulse-repetition rates based on the intensity information.

In some such embodiments, the method further includes delivering an electrical signal to the plurality of neurons of the cochlea and/or the vestibular system, such that a combination of the electrical signal and the light signals stimulate the nerve action potentials in the plurality of neurons. In some embodiments, the present invention uses electrical sources where appropriate for widespread stimulation (either using a higher-signal-strength electrical stimulation alone to trigger widespread NAPs in surrounding tissue, and/or using a lower-signal-strength electrical stimulation signal to sensitize the nearby tissue in order to reduce the optical power needed to trigger NAPs) and utilizes optical signal sources for triggering the frequency-specific "spikes". This allows for power-supply savings by limiting (i.e., reducing) the use of the optical sources for triggering NAPs in response to sensed broadband audio signals (audio signals having many different frequency components), and better replication (improved fidelity of the hearing sensation of the patient) of the audio signal content by using the characteristics of both electrical and optical stimulation when only one or just a few frequency components are sensed. In some embodiments, the electrical and optical stimulation sources are connected to and driven by the output of a signal processor whose input is coupled to signals from both an acoustic-detector device (e.g., in some embodiments, a device such as are typically used for electrical-stimulation cochlear implants) and to signals from a balance-sensing device (e.g., a gyroscope, accelerometer, or the like). In some embodiments, the signal-processor device processes the acoustic and balance information and separates the signals into two or more groups, including at least one with broadband characteristics and at least one with narrow band characteristics. The device then selectively activates the electrical and optical sources based at least in part on the broadband and narrow-band groups.

In some embodiments, the present invention provides a method for stimulating neurons of a cochlea and/or vestibular system of a patient to provide sensations for the patient. This method includes generating a plurality of light signals that have different wavelengths and that, when applied to a neuron of a person, can stimulate a nerve action potential in the neuron; generating sensitizing signals that, when applied to a neuron of a person, can sensitize the neuron to trigger a nerve action potential in the neuron upon an additional application of light to the neuron; delivering the sensitizing signals to a plurality of neurons of the cochlea and/or vestibular system of the patient; delivering the generated light signals to a plurality of neurons of the cochlea and/or the vestibular system of the patient; and selectively controlling the plurality of light signals to optically stimulate the plurality of neurons in order to control nerve action potentials (NAPs) produced by the plurality of neurons. In some embodiments, the sensitizing signals include sub-threshold electrical signals (signals that alone have a low probability (e.g., in some embodiments, less than 25% probability of triggering a NAP from one such sub-threshold electrical signal, or in other embodiments, less than 33%, 20%, 10%, 5% or 2% probability of triggering a NAP from one such sub-threshold electrical signal) that reduce the amount of optical energy needed to reliably trigger a NAP.

Some embodiments of the method further include further comprising sensing one or more conditions that affect balance, wherein the selectively controlling the plurality of light signals includes controlling the light signals, at least partly based on the sensed one or more conditions that affect balance, to provide a sense-of-balance nerve stimulation to the vestibular system of the patient; receiving an audio signal; and processing the received audio signal to obtain audio frequency and intensity information, wherein the delivering of at least a portion of the plurality of light signals comprises delivering the light pulses to the cochlea of the person, and wherein the selectively controlling of the light signals includes selectively controlling the light signals to emit light pulses to selected locations of the cochlea of the person based on the frequency information and at selected pulse-repetition rates based on the intensity information.

In some embodiments, the delivering of light signals further includes delivering infrared light from a laser. In some embodiments, the delivering of light signals further includes delivering infrared light from a vertical-cavity surface-emitting laser (VCSEL).

In some embodiments, the present invention provides an apparatus that includes a cochlear-implant portion, wherein the cochlear-implant portion includes a first plurality of independently controllable light sources that are configured to generate a first plurality of light signals, including a first light signal and a second light signal, that, when applied to a cochlear neuron of the person, each stimulate a nerve action potential (NAP) in the cochlear neuron, a first transmission medium configured to transmit the first plurality of light signals from the first plurality of light sources to one or more neurons in the cochlea in order to trigger NAPs in the one or more neurons of the cochlea; a vestibular-implant portion, wherein the vestibular-implant portion includes a second plurality of independently controllable light sources that are configured to generate a second plurality of light signals, including a third light signal and a fourth light signal, that, when applied to a vestibular neuron of a vestibular system of the person, each stimulate a nerve action potential (NAP) in the vestibular neuron, a second transmission medium configured to transmit the second plurality of light signals from the second plurality of light sources to one or more neurons in the vestibular system in order to trigger NAPs in the one or more neurons of the vestibular system; and a controller operatively coupled to the cochlear-implant portion to selectively control the first plurality of light signals from each of the first plurality of light sources such that the first plurality of light signals provide controlled optical stimulation to the one or more of neurons of the cochlea in order to control nerve action potentials (NAPs) produced by the one or more neurons of the cochlea, and operatively coupled to the vestibular-implant portion to selectively control the second plurality of light signals from each of the second plurality of light sources such that the second plurality of light signals provide controlled optical stimulation to the one or more of neurons of the vestibular system in order to control nerve action potentials (NAPs) produced by the one or more neurons of the vestibular system.

In some embodiments of the apparatus, control of the light signals provided by the controller includes selective control of a duty cycle of the plurality of light signals. In some embodiments of the apparatus, the control of the light signals provided by the controller includes selective control of a wavelength of the plurality of light signals. In some embodiments of the apparatus, the first and second transmission media include a plurality of data channels (i.e., input and/or output channels (called "I/Os")). In some embodiments, the first and second transmission media include a plurality of optical fibers, each having a conductive material (e.g., a metal film) applied to a surface of the optical fiber, wherein the conductive material is in turn covered with an insulator (e.g., a polymer coating, and/or a silicon oxide and/or silicon nitride insulator layer), and optionally one or more additional conductive layers further coated by additional insulator layers to provide a coaxially shielded electrical conductor that is formed directly on the optical fiber, and wherein the optical fiber is used to deliver the optical stimulation pulses and the one or more electrical conductors are used to transmit electrical stimulation or pre-conditioning electrical energy to the tissue being stimulated. In some embodiments, the electrical conductors are also used to carry electrical signals sensed from the neurons of the patient (e.g., NAP signals in the nerve pathways are detected electrically using the conductors formed on the optical fibers).

In some embodiments of the apparatus, the first and second transmission media include a plurality of optical fibers each of which carries a different signal. In some such embodiments, the plurality of optical fibers each have one or more electrical conductors formed thereon, wherein each of a plurality of the electrical conductors carry a different signal. In some embodiments of the apparatus, the first and second transmission media include an optical fiber. In some embodiments of the apparatus, the first and second transmission media include a lens. In some embodiments of the apparatus, the first and second transmission media delivers the first and second plurality of light signals from the first and second plurality of light sources without using an optical fiber or a lens.

Some embodiments of the apparatus further includes a microphone having a signal output operatively coupled to a first wireless transmitter that is configured to transmit information based on the microphone signal to the controller, and the apparatus further includes a balance-detection device having a signal output operatively coupled to a second wireless transmitter that is configured to transmit information based on the balance signal to the controller.

In some embodiments, the present invention provides an apparatus that includes a cochlear-implant portion, wherein the cochlear-implant portion includes a first plurality of independently controllable light sources that are configured to generate a first plurality of light signals, including a first light signal and a second light signal, that, when applied to a cochlear neuron of the person while the cochlear neuron is sensitized, each will stimulate a nerve action potential (NAP) in the cochlear neuron, a first sensitizing-signal generator that generates a first plurality of sensitizing signals, including a first sensitizing signal and a second sensitizing signal, that, when applied to the cochlear neuron of the person, will sensitize the neuron to trigger a NAP in the neuron upon application of one or more of the plurality light signals to the neuron; a transmission medium configured to transmit the first light signal from the first plurality of light sources to one or more cochlear neurons of a first auditory nerve pathway of the person, and to transmit the second light signal from the plurality of light sources to one or more neurons of a second auditory nerve pathway of the person; a vestibular-implant portion that includes a second plurality of independently controllable light sources that are configured to generate a second plurality of light signals, including a third light signal and a fourth light signal, that, when applied to a vestibular neuron of the person while the vestibular neuron is sensitized, each will stimulate a nerve action potential (NAP) in the vestibular neuron, a second sensitizing-signal generator that generates a second plurality of sensitizing signals, including a third sensitizing signal and a fourth sensitizing signal, that, when applied to the vestibular neuron of the person, will sensitize the vestibular neuron to trigger a NAP in the vestibular neuron upon application of one or more of the second plurality light signals to the vestibular neuron; a transmission medium configured to transmit the third light signal from the second plurality of light sources to one or more vestibular neurons of a first vestibular nerve pathway of the person, and to transmit the fourth light signal from the second plurality of light sources to one or more vestibular neurons of a second vestibular nerve pathway.

It is specifically contemplated that the present invention includes embodiments having combinations and subcombinations of the various embodiments and features that are individually described herein, including the various embodiments described by patent applications and patents incorporated by reference herein (i.e., rather than listing every combinatorial of the elements, this specification includes descriptions of representative embodiments and contemplates embodiments that include some of the features from one embodiment combined with some of the features of another embodiment). Further, some embodiments include fewer than all the components described as part of any one of the embodiments described herein.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for stimulating nerve-action potentials (NAPs) in each one of a plurality of cochlear neurons in a cochlea of a person and in each one of a plurality of vestibular neurons in a vestibular organ of the person in order to provide auditory and balance sensations for the person, the apparatus comprising:
   a cochlear-implant portion, wherein the cochlear-implant portion includes:
      a first plurality of independently controllable light sources that are configured to generate a first plurality of light signals, including a first light signal and a second light signal, that, when applied to a selected one of the plurality of cochlear neurons, each stimulate a nerve action potential (NAP) in the selected cochlear neuron, and
      a first transmission medium configured to be inserted into the cochlea and to transmit the first plurality of light signals from the first plurality of light sources to the selected cochlear neuron from inside the cochlea in order to trigger NAPs in the selected cochlear neuron;
   a vestibular-implant portion, wherein the vestibular-implant portion includes:
      a second plurality of independently controllable light sources that are configured to generate a second plurality of light signals, including a third light signal and a fourth light signal, that, when applied to a selected one of the plurality of vestibular neurons of a vestibular system of the person, each stimulate a nerve action potential (NAP) in the selected vestibular neuron, and
      a second transmission medium configured to transmit the second plurality of light signals from the second plurality of light sources to the selected vestibular neuron in order to trigger NAPs in the selected vestibular neuron; and
   a controller operatively coupled to the cochlear-implant portion to selectively control the first plurality of light signals from each of the first plurality of light sources such that the first plurality of light signals provide controlled optical stimulation to the selected cochlear neuron in order to trigger nerve action potentials (NAPs) produced by the selected cochlear neuron, and wherein the controller is also operatively coupled to the vestibular-implant portion to selectively control the second plurality of light signals from each of the second plurality of light sources such that the second plurality of light signals provide controlled optical stimulation to the selected vestibular neuron in order to trigger nerve action potentials (NAPs) produced by the selected vestibular neuron.

2. The apparatus of claim 1, further comprising:
   an audio-signal sensor configured to receive an audio signal and transmit an audio-controller-input signal to the controller based on the received audio signal; and
   an orientation-signal sensor configured to receive an orientation signal and transmit an orientation-controller-input signal to the controller based on the received orientation signal, wherein the controller is further configured to receive the audio-controller-input signal and the orientation-controller-input signal to obtain audio information and orientation information, wherein the controller is further configured to control the first plurality of light signals to emit light pulses to selected locations of the cochlea based on the audio information, and wherein the controller is further configured to control the second plurality of light signals to emit light pulses to selected locations of the vestibular organ based on the orientation information.

3. The apparatus of claim 1, wherein the second plurality of light sources is configured to generate a third plurality of light signals that, when applied to the selected vestibular neuron of the person, reduces a background-NAP rate in the selected vestibular neuron;
   wherein the second transmission medium is further configured to deliver the third plurality of light signals to the selected vestibular neuron during a second period of time; and
   wherein the controller is further configured to selectively control the third plurality of light signals to reduce the background-NAP rate of the selected vestibular neuron during the second period of time.

4. The apparatus of claim 3, further comprising a background sensor configured to detect a background-NAP rate associated with the selected vestibular neuron and transmit a background-NAP-rate signal to the controller,
   wherein the controller is further configured to process the received background-NAP-rate signal to obtain the background-NAP rate, and wherein the controller is further configured to control the third plurality of light signals to reduce the background-NAP rate of the selected vestibular neuron during the second time period based on the received background-NAP-rate signal.

5. The apparatus of claim 1, further comprising:
   a first plurality of electrodes configured to generate a first plurality of electrical signals that, when applied to the plurality of cochlear neurons including the selected cochlear neuron, sensitize the plurality of cochlear neurons;

a third transmission medium configured to deliver the first plurality of electrical signals to the plurality of cochlear neurons;

a second plurality of electrodes configured to generate a second plurality of electrical signals that, when applied to the plurality of vestibular neurons including the selected vestibular neuron, sensitize the plurality of vestibular neurons;

a fourth transmission medium configured to deliver the second plurality of light signals to the plurality of vestibular neurons, wherein the controller is further configured to selectively control the first and second plurality of electrical signals to sensitize the plurality of cochlear neurons and the plurality of vestibular neurons in order to control NAPs of the selected cochlear neuron and the selected vestibular neuron, but wherein others of the plurality of sensitized cochlear and vestibular neurons are not optically stimulated such that NAPs are not triggered in those other sensitized cochlear and vestibular neurons.

6. The apparatus of claim 1, wherein the first plurality of independently controllable light sources includes a plurality of vertical-cavity surface-emitting lasers (VCSELs).

7. The apparatus of claim 1, wherein the controller is further configured to selectively change a wavelength of the first and second plurality of light signals to be a selected one of a plurality of selectable wavelengths.

8. The apparatus of claim 1, wherein the controller is further configured to selectively control a duty cycle of the first and second plurality of light signals.

9. The apparatus of claim 1, wherein the first transmission medium includes a plurality of optical fibers, each having a conductive material applied to a surface of the optical fiber.

10. The apparatus of claim 1, wherein the first transmission medium includes a lens and an optical fiber optically coupled to the lens.

11. The apparatus of claim 1, wherein the first transmission medium includes a plurality of parallel optical-signal-transmission waveguides.

12. The apparatus of claim 1, wherein the first transmission medium is further configured to transmit a first pulsed light signal at a first time, wherein the second transmission medium is further configured to transmit a second pulsed light signal at a second time, and wherein the controller is further configured to interleave the transmission of the pulsed light signals generated by the first plurality of light sources and the second plurality of light sources, wherein the first time is different than the second time.

13. An apparatus for stimulating nerve-action potentials (NAPs) in each one of a plurality of cochlear neurons in a cochlea of a person and in each one of a plurality of vestibular neurons in a vestibular organ of the person in order to provide auditory and balance sensations for the person, the apparatus comprising:

a cochlear-implant portion, wherein the cochlear-implant portion includes:

a first plurality of independently controllable light sources that are configured to generate a first plurality of light signals, including a first light signal and a second light signal, that, when applied to a selected one of the plurality of cochlear neurons, each stimulate a nerve action potential (NAP) in the selected cochlear neuron, and a first transmission medium configured to transmit the first plurality of light signals from the first plurality of light sources to the selected cochlear neuron in order to trigger NAPs in the selected cochlear neuron;

a vestibular-implant portion, wherein the vestibular-implant portion includes:

a second plurality of independently controllable light sources that are configured to generate a second plurality of light signals, including a third light signal and a fourth light signal, that, when applied to a selected one of the plurality of vestibular neurons of a vestibular system of the person, each stimulate a nerve action potential (NAP) in the selected vestibular neuron, and a second transmission medium configured to transmit the second plurality of light signals from the second plurality of light sources to the selected vestibular neuron in order to trigger NAPs in the selected vestibular neuron;

a controller operatively coupled to the cochlear-implant portion to selectively control the first plurality of light signals from each of the first plurality of light sources such that the first plurality of light signals provide controlled optical stimulation to the selected cochlear neuron in order to trigger nerve action potentials (NAPs) produced by the selected cochlear neuron, and wherein the controller is also operatively coupled to the vestibular-implant portion to selectively control the second plurality of light signals from each of the second plurality of light sources such that the second plurality of light signals provide controlled optical stimulation to the selected vestibular neuron in order to trigger nerve action potentials (NAPs) produced by the selected vestibular neuron; and an audio-signal sensor configured to receive an audio signal and transmit an audio-controller-input signal to the controller based on the received audio signal, wherein the controller is further configured to receive the audio-controller-input signal to obtain audio information, wherein the controller is further configured to control the first plurality of light signals to emit light pulses to selected locations of the cochlea based on the audio information.

14. The apparatus of claim 13, wherein the second plurality of light sources is configured to generate a third plurality of light signals that, when applied to the selected vestibular neuron of the person, reduces a background-NAP rate in the selected vestibular neuron;

wherein the second transmission medium is further configured to deliver the third plurality of light signals to the selected vestibular neuron during a second period of time; and wherein the controller is further configured to selectively control the third plurality of light signals to reduce the background-NAP rate of the selected vestibular neuron during the second period of time.

15. The apparatus of claim 13, further comprising:

a first plurality of electrodes configured to generate a first plurality of electrical signals that, when applied to the plurality of cochlear neurons including the selected cochlear neuron, sensitize the plurality of cochlear neurons;

a third transmission medium configured to deliver the first plurality of electrical signals to the plurality of cochlear neurons;

a second plurality of electrodes configured to generate a second plurality of electrical signals that, when applied to the plurality of vestibular neurons including the selected vestibular neuron, sensitize the plurality of vestibular neurons;
a fourth transmission medium configured to deliver the second plurality of light signals to the plurality of vestibular neurons,
wherein the controller is further configured to selectively control the first and second plurality of electrical signals to sensitize the plurality of cochlear neurons and the plurality of vestibular neurons in order to control NAPs of the selected cochlear neuron and the selected vestibular neuron, but wherein others of the plurality of sensitized cochlear and vestibular neurons are not optically stimulated such that NAPs are not triggered in those other sensitized cochlear and vestibular neurons.

16. The apparatus of claim 13, wherein the first transmission medium is further configured to transmit a first pulsed light signal at a first time, wherein the second transmission medium is further configured to transmit a second pulsed light signal at a second time, and wherein the controller is further configured to interleave the transmission of the pulsed light signals generated by the first plurality of light sources and the second plurality of light sources, wherein the first time is different than the second time.

17. An apparatus for stimulating nerve-action potentials (NAPs) in each one of a plurality of cochlear neurons in a cochlea of a person and in each one of a plurality of vestibular neurons in a vestibular organ of the person in order to provide auditory and balance sensations for the person, the apparatus comprising:
a cochlear-implant portion, wherein the cochlear-implant portion includes:
a first plurality of independently controllable light sources that are configured to generate a first plurality of light signals, including a first light signal and a second light signal, that, when applied to a selected one of the plurality of cochlear neurons, each stimulate a nerve action potential (NAP) in the selected cochlear neuron, and
a first transmission medium configured to transmit the first plurality of light signals from the first plurality of light sources to the selected cochlear neuron in order to trigger NAPs in the selected cochlear neuron;
a vestibular-implant portion, wherein the vestibular-implant portion includes:
a second plurality of independently controllable light sources that are configured to generate a second plurality of light signals, including a third light signal and a fourth light signal, that, when applied to a selected one of the plurality of vestibular neurons of a vestibular system of the person, each stimulate a nerve action potential (NAP) in the selected vestibular neuron, and
a second transmission medium configured to transmit the second plurality of light signals from the second plurality of light sources to the selected vestibular neuron in order to trigger NAPs in the selected vestibular neuron;
a controller operatively coupled to the cochlear-implant portion to selectively control the first plurality of light signals from each of the first plurality of light sources such that the first plurality of light signals provide controlled optical stimulation to the selected cochlear neuron in order to trigger nerve action potentials (NAPs) produced by the selected cochlear neuron, and wherein the controller is also operatively coupled to the vestibular-implant portion to selectively control the second plurality of light signals from each of the second plurality of light sources such that the second plurality of light signals provide controlled optical stimulation to the selected vestibular neuron in order to trigger nerve action potentials (NAPs) produced by the selected vestibular neuron; and
an orientation-signal sensor configured to receive an orientation signal and transmit an orientation-controller-input signal to the controller based on the received orientation signal, wherein the controller is further configured to receive the orientation-controller-input signal to obtain orientation information, wherein the controller is further configured to control the second plurality of light signals to emit light pulses to selected locations of the vestibular organ based on the orientation information.

18. The apparatus of claim 17, wherein the second plurality of light sources is configured to generate a third plurality of light signals that, when applied to the selected vestibular neuron of the person, reduces a background-NAP rate in the selected vestibular neuron;
wherein the second transmission medium is further configured to deliver the third plurality of light signals to the selected vestibular neuron during a second period of time; and
wherein the controller is further configured to selectively control the third plurality of light signals to reduce the background-NAP rate of the selected vestibular neuron during the second period of time.

19. The apparatus of claim 17, further comprising:
a first plurality of electrodes configured to generate a first plurality of electrical signals that, when applied to the plurality of cochlear neurons including the selected cochlear neuron, sensitize the plurality of cochlear neurons;
a third transmission medium configured to deliver the first plurality of electrical signals to the plurality of cochlear neurons;
a second plurality of electrodes configured to generate a second plurality of electrical signals that, when applied to the plurality of vestibular neurons including the selected vestibular neuron, sensitize the plurality of vestibular neurons;
a fourth transmission medium configured to deliver the second plurality of light signals to the plurality of vestibular neurons,
wherein the controller is further configured to selectively control the first and second plurality of electrical signals to sensitize the plurality of cochlear neurons and the plurality of vestibular neurons in order to control NAPs of the selected cochlear neuron and the selected vestibular neuron, but wherein others of the plurality of sensitized cochlear and vestibular neurons are not optically stimulated such that NAPs are not triggered in those other sensitized cochlear and vestibular neurons.

20. The apparatus of claim 17, wherein the first transmission medium is further configured to transmit a first pulsed light signal at a first time, wherein the second transmission medium is further configured to transmit a second pulsed light signal at a second time, and wherein the controller is further configured to interleave the transmission of the pulsed light signals generated by the first plurality of light sources and the second plurality of light sources, wherein the first time is different than the second time.

* * * * *